US011135281B2

(12) United States Patent
Clements et al.

(10) Patent No.: US 11,135,281 B2
(45) Date of Patent: Oct. 5, 2021

(54) WEST NILE VIRUS VACCINE AND METHOD OF USE THEREOF

(71) Applicants: Hawaii Biotech Inc., Honolulu, HI (US); Infectious Disease Research Institute, Seattle, WA (US)

(72) Inventors: David E. Clements, Honolulu, HI (US); Neal Van Hoeven, Seattle, WA (US)

(73) Assignees: Hawaii Biotech, Inc., Honolulu, HI (US); Infectious Disease Research Institute, Seattle, WA (US)

(*) Notice: Subject to any disclaimer, the term of this patent is extended or adjusted under 35 U.S.C. 154(b) by 0 days.

(21) Appl. No.: 16/315,986

(22) PCT Filed: Jul. 7, 2017

(86) PCT No.: PCT/US2017/041173
§ 371 (c)(1),
(2) Date: Jan. 7, 2019

(87) PCT Pub. No.: WO2018/009850
PCT Pub. Date: Jan. 11, 2018

(65) Prior Publication Data
US 2019/0298819 A1 Oct. 3, 2019

Related U.S. Application Data

(60) Provisional application No. 62/404,694, filed on Oct. 5, 2016, provisional application No. 62/359,989, filed on Jul. 8, 2016.

(51) Int. Cl.

| | |
|---|---|
| *A61K 39/12* | (2006.01) |
| *A61K 31/14* | (2006.01) |
| *A61K 9/127* | (2006.01) |
| *A61K 39/39* | (2006.01) |
| *A61P 31/14* | (2006.01) |
| *A61K 36/00* | (2006.01) |
| *A61K 36/73* | (2006.01) |
| *A61K 39/00* | (2006.01) |

(52) U.S. Cl.
CPC .............. *A61K 39/12* (2013.01); *A61K 9/127* (2013.01); *A61K 36/00* (2013.01); *A61K 36/73* (2013.01); *A61K 39/39* (2013.01); *A61P 31/14* (2018.01); *A61K 2039/55505* (2013.01); *A61K 2039/55566* (2013.01); *A61K 2039/55572* (2013.01); *A61K 2039/55577* (2013.01); *C12N 2770/24134* (2013.01)

(58) Field of Classification Search
None
See application file for complete search history.

(56) References Cited

U.S. PATENT DOCUMENTS

2005/0287170 A1* 12/2005 Lieberman ......... C07K 16/1081 424/204.1
2012/0141520 A1 6/2012 Coller et al.
2012/0301502 A1 11/2012 Caulfield et al.

FOREIGN PATENT DOCUMENTS

WO WO 2006/115548 A2 11/2006

OTHER PUBLICATIONS

Putnaketal., An evaluation of dengue type-2 inactivated, recombinant subunit, and live-attenuated vaccine candidates in the rhesus macaque model, 2005, Vaccine, vol. 23, pp. 4442-4452.*
Lieberman et al., Immunogenicity and Protective Efficacy of a Recombinant Subunit West Nile Virus Vaccine in Rhesus Monkeys, Clinical and Vaccine Immunology, 2009, vol. 16, No. 9, pp. 1332-1337.*
Lieberman et al., "Preparation and Immunogenic Properties of a Recombinant West Nile Subunit Vaccine," *Vaccine* (2007), 25(3):414-423.
Van Hoeven et al., "A Novel Synthetic TLR-4 Agonist Adjuvant Increases the Protective Response to a Clinical-State West Nile Virus Vaccine Antigen in Multiple Formulations," *PLoS ONE* (2016), 11:1-20, e0149610.
Baldwin, Susan L. et al.: "*Synthetic TLR4 agonists enhance functional antibodies and CD4+ T-cell responses against the Plasmodium falciparum GMZ2.6C multi-stage vaccine antigen*"; VACCINE, vol. 34, No. 19, Mar. 17, 2016, pp. 2207-2215. XP029510147.
Extended European Search Report dated Feb. 28, 2020, regarding EP 17 825 014.
Garcon, Nathalie et al: "*Recent clinical experience with vaccines using MPL- and QS-21-containing adjuvant systems*"; Expert Review of Vaccines, vol. 10, No. 4, Apr. 1, 2011, pp. 471-486. XP009176124.

* cited by examiner

*Primary Examiner* — Benjamin P Blumel
(74) *Attorney, Agent, or Firm* — DLA Piper LLP (US)

(57) ABSTRACT

A West Nile virus (WNV) vaccine for human use is described that contains a recombinantly produced form of truncated WNV envelope glycoprotein and a combination of a Toll-like receptor 4 (TLR-4) and saponin adjuvants. A pharmaceutically acceptable vehicle may also be included in the vaccine.

16 Claims, 32 Drawing Sheets

Specification includes a Sequence Listing.

```
Phe Asn Cys Leu Gly Met Ser Asn Arg Asp Phe Leu Glu Gly Val
1               5                   10                  15

Ser Gly Ala Thr Trp Val Asp Leu Val Leu Glu Gly Asp Ser Cys
                20                  25                  30

Val Thr Ile Met Ser Lys Asp Lys Pro Thr Ile Asp Val Lys Met
                35                  40                  45

Met Asn Met Glu Ala Ala Asn Leu Ala Glu Val Arg Ser Tyr Cys
                50                  50                  60

Tyr Leu Ala Thr Val Ser Asp Leu Ser Thr Lys Ala Ala Cys Pro
                65                  70                  75

Thr Met Gly Glu Ala His Asn Asp Lys Arg Ala Asp Pro Ala Phe
                80                  85                  90

Val Cys Arg Gln Gly Val Val Asp Arg Gly Trp Gly Asn Gly Cys
                95                  100                 105

Gly Leu Phe Gly Lys Gly Ser Ile Asp Thr Cys Ala Lys Phe Ala
                110                 115                 120

Cys Ser Thr Lys Ala Ile Gly Arg Thr Ile Leu Lys Glu Asn Ile
                125                 130                 135

Lys Tyr Glu Val Ala Ile Phe Val His Gly Pro Thr Thr Val Glu
                140                 145                 150
```

FIG. 8

```
Ser His Gly Asn Tyr Ser Thr Gln Val Gly Ala Thr Gln Ala Gly
            155                 160                 165

Arg Phe Ser Ile Thr Pro Ala Ala Pro Ser Tyr Thr Leu Lys Leu
            170                 175                 180

Gly Glu Tyr Gly Glu Val Thr Val Asp Cys Glu Pro Arg Ser Gly
            185                 190                 195

Ile Asp Thr Asn Ala Tyr Tyr Val Met Thr Val Gly Thr Lys Thr
            200                 205                 210

Phe Leu Val His Arg Glu Trp Phe Met Asp Leu Asn Leu Pro Trp
            215                 220                 225

Ser Ser Ala Gly Ser Thr Val Trp Arg Asn Arg Glu Thr Leu Met
            230                 235                 240

Glu Phe Glu Glu Pro His Ala Thr Lys Gln Ser Val Ile Ala Leu
            245                 250                 255

Gly Ser Gln Glu Gly Ala Leu His Gln Ala Leu Ala Gly Ala Ile
            260                 265                 270

Pro Val Glu Phe Ser Ser Asn Thr Val Lys Leu Thr Ser Gly His
            275                 280                 285

Leu Lys Cys Arg Val Lys Met Glu Lys Leu Gln Leu Lys Gly Thr
            290                 295                 300
```

FIG. 8 (cont.)

```
Thr Tyr Gly Val Cys Ser Lys Ala Phe Lys Phe Leu Gly Thr Pro
            305                 310                 315

Ala Asp Thr Gly His Gly Thr Val Val Leu Glu Leu Gln Tyr Thr
            320                 325                 330

Gly Thr Asp Gly Pro Cys Lys Val Pro Ile Ser Ser Val Ala Ser
            335                 340                 345

Leu Asn Asp Leu Thr Pro Val Gly Arg Leu Val Thr Val Asn Pro
            350                 355                 360

Phe Val Ser Val Ala Thr Ala Asn Ala Lys Val Leu Ile Glu Leu
            365                 370                 375

Glu Pro Pro Phe Gly Asp Ser Tyr Ile Val Val Gly Arg Gly Glu
            380                 385                 390

Gln Gln Ile Asn His His Trp His Lys Ser Gly
            395                 400
```

FIG. 8 (cont.)

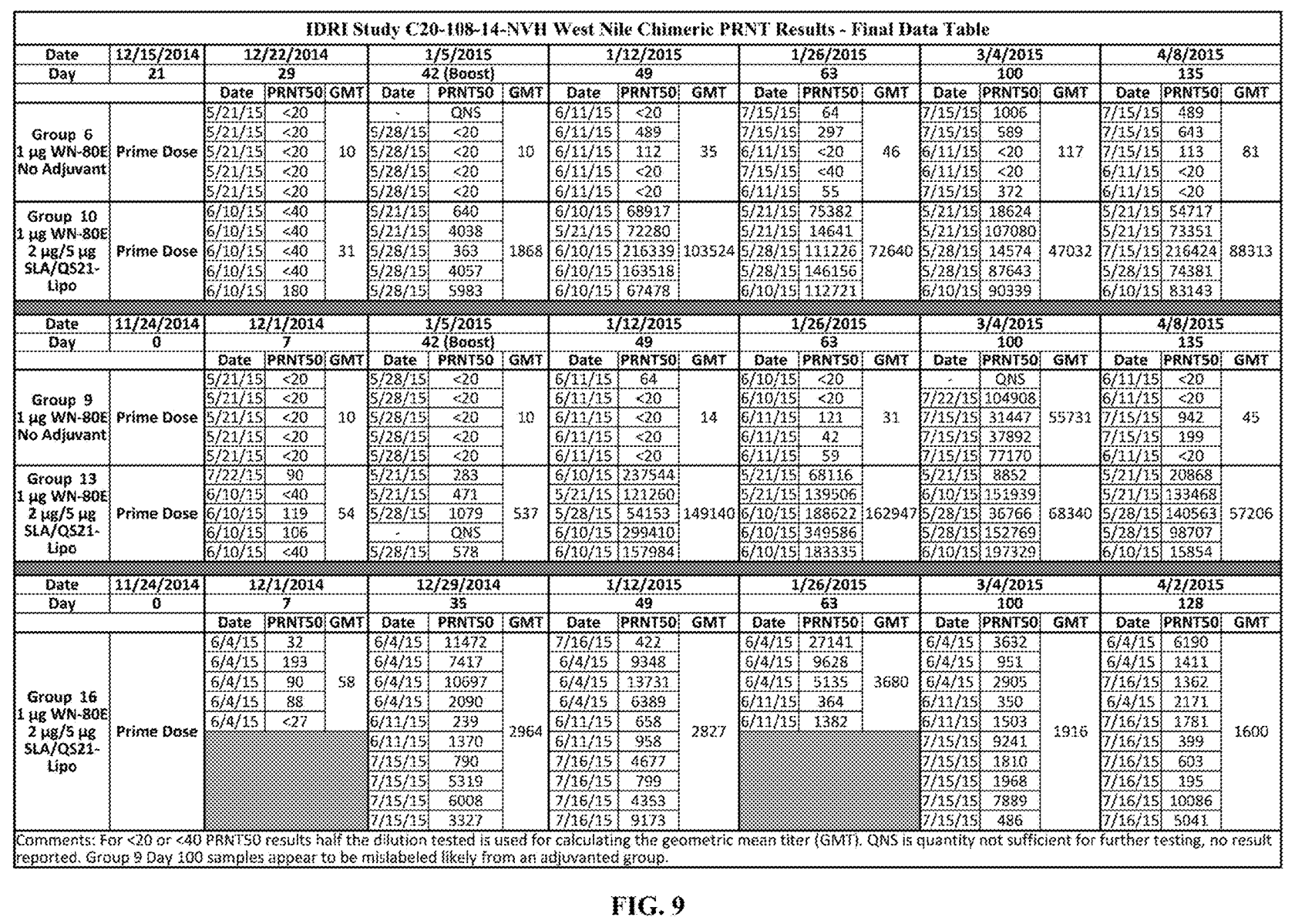

IDRI Study C20-108-14-NVH West Nile Chimeric PRNT Results – Final Data Table

| Date | | 12/15/2014 | | 12/22/2014 | | | 1/5/2015 42 (Boost) | | | 1/12/2015 | | | 1/26/2015 | | | 3/4/2015 | | | 4/8/2015 | | |
|---|---|---|---|---|---|---|---|---|---|---|---|---|---|---|---|---|---|---|---|---

FIG. 10

Induction of Germinal Centers Correlates with Increased WN-80E Specific Serum IgG and PRNT Titers (ID-C20-100-14)

*Based on Neutralizing Antibody Titer Induction and GC B-Cell Induction 2μg QS21 Dose Selected*

* $p < 0.05$
** $p < 0.005$
*** $p < 0.0005$
**** $p < 0.0001$ (ANOVA)

SLA and QS21 formulated in neutral liposomes demonstrated rapid induction of WNV neutralizing antibodies (D7 Post-Prime), and generated high titer antibodies following boost immunization (d42).

| C20-118-15-NVH: Hamster Challenge Study |||||
|---|---|---|---|---|
| West Nile Chimeric Virus PRNT Results for Post Dose 1 Serum |||||
| Experimental Group | Animal # | PRNT Date | PRNT$_{50}$ | GMT Values[1] | GMT |

| Experimental Group | Animal # | PRNT Date | PRNT$_{50}$ | GMT Values[1] | GMT |
|---|---|---|---|---|---|
| Group 1<br>Antigen: Saline<br>Antigen Dose: N/A<br><br>Adjuvant: None<br>Adjuvant Dose: None | 1 | 03-Sep-15 | <40 | 20 | 11 |
| | 2 | 03-Sep-15 | <20 | 10 | |
| | 3 | 03-Sep-15 | <20 | 10 | |
| | 4 | 03-Sep-15 | <20 | 10 | |
| | 5 | 03-Sep-15 | <20 | 10 | |
| | 6 | 03-Sep-15 | <20 | 10 | |
| | 7 | N/A | QNS | - | |
| | 8 | 03-Sep-15 | <20 | 10 | |
| | 9 | 03-Sep-15 | <20 | 10 | |
| | 10 | 22-Oct-15 | <20 | 10 | |
| | 11 | 22-Oct-15 | <20 | 10 | |
| | 12 | 22-Oct-15 | <20 | 10 | |
| Group 2<br>Antigen: WN-80E<br>Antigen Dose: 10 µg<br><br>Adjuvant: Saline<br>Adjuvant Dose: N/A | 1 | 03-Sep-15 | <20 | 10 | 10 |
| | 2 | 03-Sep-15 | <20 | 10 | |
| | 3 | 03-Sep-15 | <20 | 10 | |
| | 4 | 03-Sep-15 | <20 | 10 | |
| | 5 | 03-Sep-15 | <20 | 10 | |
| | 6 | 03-Sep-15 | <20 | 10 | |
| | 7 | 03-Sep-15 | <20 | 10 | |
| | 8 | N/A | QNS | - | |
| | 9 | 03-Sep-15 | <20 | 10 | |
| | 10 | N/A | QNS | - | |
| | 11 | 22-Oct-15 | <20 | 10 | |
| | 12 | 22-Oct-15 | <20 | 10 | |
| Group 3<br>Antigen: WN-80E<br>Antigen Dose: 1 µg<br><br>Adjuvant: Saline<br>Adjuvant Dose: N/A | 1 | N/A | QNS | - | 12 |
| | 2 | 03-Sep-15 | <20 | 10 | |
| | 3 | 03-Sep-15 | <20 | 10 | |
| | 4 | 03-Sep-15 | <30 | 15 | |
| | 5 | 03-Sep-15 | <43 | 22 | |
| | 6 | 03-Sep-15 | <20 | 10 | |
| | 7 | 03-Sep-15 | <20 | 10 | |
| | 8 | 03-Sep-15 | <30 | 15 | |
| | 9 | 22-Oct-15 | <20 | 10 | |
| | 10 | 22-Oct-15 | <38 | 19 | |
| | 11 | 22-Oct-15 | <20 | 10 | |
| | 12 | 03-Sep-15 | <20 | 10 | |
| Group 4<br>Antigen: WN-80E<br>Antigen Dose: 0.1 µg<br><br>Adjuvant: Saline<br>Adjuvant Dose: N/A | 1 | 03-Sep-15 | <20 | 10 | 10 |
| | 2 | 03-Sep-15 | <20 | 10 | |
| | 3 | 03-Sep-15 | <20 | 10 | |
| | 4 | 03-Sep-15 | <20 | 10 | |
| | 5 | 03-Sep-15 | <20 | 10 | |
| | 6 | 03-Sep-15 | <20 | 10 | |
| | 7 | 03-Sep-15 | <20 | 10 | |
| | 8 | 03-Sep-15 | <20 | 10 | |
| | 9 | 22-Oct-15 | <33 | 17 | |
| | 10 | 22-Oct-15 | <20 | 10 | |
| | 11 | 22-Oct-15 | <20 | 10 | |
| | 12 | 22-Oct-15 | <20 | 10 | |

Comments: [1] Half of lowest dilution tested used for geometric mean titer calculations
QNS - quantity not sufficient for further testing

FIG. 25A

| C20-118-15-NVH: Hamster Challenge Study ||||||
| West Nile Chimeric Virus PRNT Results for Post Dose 1 Serum ||||||
| Experimental Group | Animal # | PRNT Date | PRNT$_{50}$ | GMT Values[1] | GMT |
| --- | --- | --- | --- | --- | --- |
| Group 5<br>Antigen: WN-80E<br>Antigen Dose: 0.01 µg<br><br>Adjuvant: Saline<br>Adjuvant Dose: N/A | 1 | 03-Sep-15 | <20 | 10 | 10 |
| | 2 | 03-Sep-15 | <20 | 10 | |
| | 3 | 03-Sep-15 | <20 | 10 | |
| | 4 | 03-Sep-15 | <20 | 10 | |
| | 5 | 03-Sep-15 | <20 | 10 | |
| | 6 | 03-Sep-15 | <20 | 10 | |
| | 7 | 03-Sep-15 | <20 | 10 | |
| | 8 | 03-Sep-15 | <20 | 10 | |
| | 9 | N/A | QNS | . | |
| | 10 | 22-Oct-15 | <20 | 10 | |
| | 11 | 22-Oct-15 | <20 | 10 | |
| | 12 | 22-Oct-15 | <20 | 10 | |
| Group 6<br>Antigen: WN-80E<br>Antigen Dose: 1 µg<br><br>Adjuvant: SLA/QS21-Liposomes<br>Adjuvant Dose: 5 µg/2 µg | 1 | 03-Sep-15 | 148 | 148 | 263 |
| | 2 | 03-Sep-15 | 428 | 428 | |
| | 3 | 03-Sep-15 | 354 | 354 | |
| | 4 | 03-Sep-15 | 235 | 235 | |
| | 5 | 03-Sep-15 | 428 | 428 | |
| | 6 | 03-Sep-15 | 666 | 666 | |
| | 7 | 03-Sep-15 | 192 | 192 | |
| | 8 | 22-Oct-15 | 58 | 58 | |
| | 9 | 22-Oct-15 | 405 | 405 | |
| | 10 | 22-Oct-15 | 505 | 505 | |
| | 11 | 22-Oct-15 | 542 | 542 | |
| | 12 | 22-Oct-15 | 59 | 59 | |
| Group 7<br>Antigen: WN-80E<br>Antigen Dose: 0.1 µg<br><br>Adjuvant: SLA/QS21-Liposomes<br>Adjuvant Dose: 5 µg/2 µg | 1 | 03-Sep-15 | 239 | 239 | 186 |
| | 2 | 03-Sep-15 | 180 | 180 | |
| | 3 | 22-Oct-15 | 457 | 457 | |
| | 4 | 03-Sep-15 | 569 | 569 | |
| | 5 | 03-Sep-15 | 69 | 69 | |
| | 6 | 22-Oct-15 | <40 | 20 | |
| | 7 | 03-Sep-15 | 2533 | 2533 | |
| | 8 | 22-Oct-15 | 150 | 150 | |
| | 9 | 22-Oct-15 | 271 | 271 | |
| | 10 | 22-Oct-15 | 268 | 268 | |
| | 11 | 22-Oct-15 | 206 | 206 | |
| | 12 | 22-Oct-15 | <40 | 20 | |
| Group 8<br>Antigen: WN-80E<br>Antigen Dose: 0.01 µg<br><br>Adjuvant: SLA/QS21-Liposomes<br>Adjuvant Dose: 5 µg/2 µg | 1 | 03-Sep-15 | <40 | 20 | 36 |
| | 2 | 03-Sep-15 | 77 | 77 | |
| | 3 | 03-Sep-15 | <40 | 20 | |
| | 4 | 03-Sep-15 | 119 | 119 | |
| | 5 | 03-Sep-15 | 48 | 48 | |
| | 6 | 03-Sep-15 | <57 | 29 | |
| | 7 | 03-Sep-15 | <40 | 20 | |
| | 8 | 22-Oct-15 | <160 | 80 | |
| | 9 | 22-Oct-15 | <40 | 20 | |
| | 10 | 22-Oct-15 | <40 | 20 | |
| | 11 | 22-Oct-15 | 67 | 67 | |
| | 12 | 22-Oct-15 | <40 | 20 | |
| Comments: [1] Half of lowest dilution tested used for geometric mean titer calculations ||||||
| QNS - quantity not sufficient for further testing ||||||

FIG. 25B

Study C20-118-15-NVH
WN Chimeric Virus PRNT Data on Post Dose 1 Serum

FIG. 26

Due to low serum volume many samples were tested at 1:40 resulting in a PRNT50 <40 which is reported as 20

SLA-LSQ Reduces Viral Replication In Serum To Undetectable Levels in a Hamster Model of WNV Disease Following Two Immunizations

SLA-LSQ Reduces Viral Replication In Serum To Undetectable Levels in a Hamster Model of WNV Disease Following A Single Immunization

SEQUENCE LISTING

```
<160> NUMBER OF SEQ ID NOS: 2

<210> SEQ ID NO 1
<211> LENGTH: 1126
<212> TYPE: PRT
<213> ORGANISM: Artificial Sequence
<220> FEATURE:
<223> OTHER INFORMATION: Synthetic

<400> SEQUENCE: 1

Pro His Glu Ala Ser Asn Cys Tyr Ser Leu Glu Gly Leu Tyr Met Glu
1               5                   10                  15

Thr Ser Glu Arg Ala Ser Asn Ala Arg Gly Ala Ser Pro Pro His Glu
            20                  25                  30

Leu Glu Gly Leu Gly Leu Tyr Val Ala Leu Ser Glu Arg Gly Leu Tyr
        35                  40                  45

Ala Leu Ala Thr His Arg Thr Arg Pro Val Ala Leu Ala Ser Pro Leu
    50                  55                  60

Glu Val Ala Leu Leu Gly Leu Gly Leu Tyr Ala Ser Pro Ser Glu
65                  70                  75                  80

Arg Cys Tyr Ser Val Ala Leu Thr His Arg Ile Leu Glu Met Glu Thr
                85                  90                  95

Ser Glu Arg Leu Tyr Ser Ala Ser Pro Leu Tyr Ser Pro Arg Thr His
            100                 105                 110

Arg Ile Leu Glu Ala Ser Pro Val Ala Leu Leu Tyr Ser Met Glu Thr
        115                 120                 125

Met Glu Thr Ala Ser Asn Met Glu Thr Gly Leu Ala Leu Ala Ala Leu
    130                 135                 140

Ala Ala Ser Asn Leu Glu Ala Leu Ala Gly Leu Val Ala Leu Ala Arg
145                 150                 155                 160

Gly Ser Glu Arg Thr Tyr Arg Cys Tyr Ser Thr Tyr Arg Leu Glu Ala
                165                 170                 175

Leu Ala Thr His Arg Val Ala Leu Ser Glu Arg Ala Ser Pro Leu Glu
            180                 185                 190

Ser Glu Arg Thr His Arg Leu Tyr Ser Ala Leu Ala Ala Leu Ala Cys
        195                 200                 205

Tyr Ser Pro Arg Thr His Arg Met Glu Thr Gly Leu Tyr Gly Leu Ala
    210                 215                 220

Leu Ala His Ile Ser Ala Ser Asn Ala Ser Pro Leu Tyr Ser Ala Arg
225                 230                 235                 240

Gly Ala Leu Ala Ala Ser Pro Pro Arg Ala Leu Ala Pro His Glu Val
                245                 250                 255
```

```
Ala Leu Cys Tyr Ser Ala Arg Gly Gly Leu Asn Gly Leu Tyr Val Ala
            260                 265                 270

Leu Val Ala Leu Ala Ser Pro Ala Arg Gly Gly Leu Tyr Thr Arg Pro
        275                 280                 285

Gly Leu Tyr Ala Ser Asn Gly Leu Tyr Cys Tyr Ser Gly Leu Tyr Leu
    290                 295                 300

Glu Pro His Glu Gly Leu Tyr Leu Tyr Ser Gly Leu Tyr Ser Glu Arg
305                 310                 315                 320

Ile Leu Glu Ala Ser Pro Thr His Arg Cys Tyr Ser Ala Leu Ala Leu
                325                 330                 335

Tyr Ser Pro His Glu Ala Leu Ala Cys Tyr Ser Glu Arg Thr His
            340                 345                 350

Arg Leu Tyr Ser Ala Leu Ala Ile Leu Glu Gly Leu Tyr Ala Arg Gly
            355                 360                 365

Thr His Arg Ile Leu Glu Leu Glu Leu Tyr Ser Gly Leu Ala Ser Asn
        370                 375                 380

Ile Leu Glu Leu Tyr Ser Thr His Arg Gly Leu Val Ala Leu Ala Leu
385                 390                 395                 400

Ala Ile Leu Glu Pro His Glu Val Ala Leu His Ile Ser Gly Leu Tyr
                405                 410                 415

Pro Arg Thr His Arg Thr His Arg Val Ala Leu Gly Leu Ser Glu Arg
            420                 425                 430

His Ile Ser Gly Leu Tyr Ala Ser Asn Thr Tyr Arg Ser Glu Arg Thr
        435                 440                 445

His Arg Gly Leu Asn Val Ala Leu Gly Leu Tyr Ala Leu Ala Thr His
    450                 455                 460

Arg Gly Leu Asn Ala Leu Ala Gly Leu Tyr Ala Arg Gly Pro His Glu
465                 470                 475                 480

Ser Glu Arg Ile Leu Glu Thr His Arg Pro Arg Ala Leu Ala Ala Leu
                485                 490                 495

Ala Pro Arg Ser Glu Arg Thr Tyr Arg Thr His Arg Leu Glu Leu Tyr
            500                 505                 510

Ser Leu Glu Gly Leu Tyr Gly Leu Thr Tyr Arg Gly Leu Tyr Gly Leu
            515                 520                 525

Val Ala Leu Thr His Arg Val Ala Leu Ala Ser Pro Cys Tyr Ser Gly
        530                 535                 540

Leu Pro Arg Ala Arg Gly Ser Glu Arg Gly Leu Tyr Ile Leu Glu Ala
545                 550                 555                 560

Ser Pro Thr His Arg Ala Ser Asn Ala Leu Ala Thr Tyr Arg Thr Tyr
                565                 570                 575

Arg Val Ala Leu Met Glu Thr Thr His Arg Val Ala Leu Gly Leu Tyr
            580                 585                 590

Thr His Arg Leu Tyr Ser Thr His Arg Pro His Glu Leu Glu Val Ala
            595                 600                 605

Leu His Ile Ser Ala Arg Gly Gly Leu Thr Arg Pro Pro His Glu Met
        610                 615                 620

Glu Thr Ala Ser Pro Leu Glu Ala Ser Asn Leu Glu Pro Arg Thr Arg
625                 630                 635                 640

Pro Ser Glu Arg Ser Glu Arg Ala Leu Ala Gly Leu Tyr Ser Glu Arg
                645                 650                 655

Thr His Arg Val Ala Leu Thr Arg Pro Ala Arg Gly Ala Ser Asn Ala
            660                 665                 670
```

```
Arg Gly Gly Leu Thr His Arg Leu Glu Met Glu Thr Gly Leu Pro His
            675                 680                 685

Glu Gly Leu Gly Leu Pro Arg His Ile Ser Ala Leu Ala Thr His Arg
690                 695                 700

Leu Tyr Ser Gly Leu Asn Ser Glu Arg Val Ala Leu Ile Leu Glu Ala
705                 710                 715                 720

Leu Ala Leu Glu Gly Leu Tyr Ser Glu Arg Gly Leu Asn Gly Leu Gly
            725                 730                 735

Leu Tyr Ala Leu Ala Leu Glu His Ile Ser Gly Leu Asn Ala Leu Ala
            740                 745                 750

Leu Glu Ala Leu Ala Gly Leu Tyr Ala Leu Ala Ile Leu Glu Pro Arg
            755                 760                 765

Val Ala Leu Gly Leu Tyr Pro His Glu Ser Glu Arg Ser Glu Arg Ala
            770                 775                 780

Ser Asn Thr His Arg Val Ala Leu Leu Tyr Ser Leu Glu Thr His Arg
785                 790                 795                 800

Ser Glu Arg Gly Leu Tyr His Ile Ser Leu Glu Leu Tyr Ser Cys Tyr
            805                 810                 815

Ser Ala Arg Gly Val Ala Leu Leu Tyr Ser Met Glu Thr Gly Leu Tyr
            820                 825                 830

Leu Tyr Ser Gly Leu Asn Leu Glu Leu Tyr Ser Gly Leu Tyr Thr His
            835                 840                 845

Arg Thr His Arg Thr Tyr Arg Gly Leu Tyr Val Ala Leu Cys Tyr Ser
            850                 855                 860

Ser Glu Arg Leu Tyr Ser Ala Leu Ala Pro His Glu Leu Glu Gly Leu
865                 870                 875                 880

Tyr Thr His Arg Pro Arg Ala Leu Ala Ala Ser Pro Thr His Arg Gly
            885                 890                 895

Leu Tyr His Ile Ser Gly Leu Tyr Thr His Arg Val Ala Leu Val Ala
            900                 905                 910

Leu Leu Glu Gly Leu Gly Leu Asn Thr Tyr Arg Thr His Arg Gly Leu
            915                 920                 925

Tyr Thr His Arg Ala Ser Pro Gly Leu Tyr Pro Arg Cys Tyr Ser Leu
            930                 935                 940

Tyr Ser Val Ala Leu Pro Arg Ile Leu Glu Glu Arg Ser Glu Arg
945                 950                 955                 960

Val Ala Leu Ala Leu Ala Ser Glu Arg Leu Glu Ala Ser Asn Ala Ser
                    965                 970                 975

Pro Leu Glu Thr His Arg Pro Arg Val Ala Leu Gly Leu Tyr Ala Arg
            980                 985                 990

Gly Leu Glu Val Ala Leu Thr His  Arg Val Ala Leu Ala  Ser Asn Pro
            995                 1000                1005

Arg Pro  His Glu Val Ala Leu  Ser Glu Arg Val Ala  Leu Ala Leu
    1010                1015                1020

Ala Thr  His Arg Ala Leu Ala  Ala Ser Asn Ala Leu  Ala Leu Tyr
    1025                1030                1035

Ser Val  Ala Leu Leu Glu Ile  Leu Glu Gly Leu Leu  Glu Gly Leu
    1040                1045                1050

Tyr Pro  Arg Pro Arg Pro His  Glu Gly Leu Tyr Ala  Ser Pro Ser
    1055                1060                1065

Glu Arg  Thr Tyr Arg Ile Leu  Glu Val Ala Leu Val  Ala Leu Gly
    1070                1075                1080

Leu Tyr  Ala Arg Gly Gly Leu  Tyr Gly Leu Gly Leu  Asn Gly Leu
```

```
                    1085                1090                1095
Asn Ile Leu Glu Ala Ser Asn His Ile Ser His Ile Ser Thr Arg
            1100                1105                1110
Pro His Ile Ser Leu Tyr Ser Ser Glu Arg Gly Leu Tyr
            1115                1120                1125

<210> SEQ ID NO 2
<211> LENGTH: 401
<212> TYPE: PRT
<213> ORGANISM: Artificial Sequence
<220> FEATURE:
<223> OTHER INFORMATION: Synthetic

<400> SEQUENCE: 2

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
    210                 215                 220

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
```

-continued

```
                325                 330                 335
Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
        355                 360                 365

Ala Lys Val Leu Ile Glu Leu Glu Pro Pro Phe Gly Asp Ser Tyr Ile
    370                 375                 380

Val Val Gly Arg Gly Glu Gln Gln Ile Asn His His Trp His Lys Ser
385                 390                 395                 400

Gly
```

WEST NILE VIRUS VACCINE AND METHOD OF USE THEREOF

CROSS-REFERENCE TO RELATED APPLICATIONS

This application is a 35 USC § 371 National Stage application of International Application No. PCT/US2017/041173 filed Jul. 7, 2017, now pending; which claims the benefit under 35 USC § 119(e) to U.S. Application Ser. No. 62/404,694 filed Oct. 5, 2016 and to U.S. Application Ser. No. 62/359,989 filed Jul. 8, 2016. The disclosure of each of the prior applications is considered part of and is incorporated by reference in the disclosure of this application.

STATEMENT OF GOVERNMENT SUPPORT

The material in the accompanying sequence listing is hereby incorporated by reference into this application. The accompanying sequence listing text file, name HBI1120_3_Substitute_Sequence_Listing.txt, was created on Apr. 22, 2020, and is 14 kb. The file can be accessed using Microsoft Word on a computer that uses Windows OS.

INCORPORATION OF SEQUENCE LISTING

The material in the accompanying sequence listing is hereby incorporated by reference into this application. The accompanying sequence listing text file, name HBI1120_3WO_Sequence_Listing, was created on Jul. 7, 2017, and is 10 kb. The file can be assessed using Microsoft Word on a computer that uses Windows OS.

BACKGROUND

Field of Invention

The present invention relates to vaccines, and more particularly to a vaccine designed to protect humans from disease caused by the West Nile virus (WNV) includes a truncated version of the recombinant envelope (E) glycoprotein from WNV in combination with a Toll-like receptor 4 (TLR-4) agonist.

Background Information

WNV is a mosquito-borne member of the family Flaviviridae that has emerged in recent years to become a serious public health threat. The virus was initially identified in the West Nile district of Uganda in 1937, and has since spread worldwide. The virus was first identified in North America in the United States in 1999, and has since spread into Canada, Mexico, as well as central and South America. Following introduction into North America, the number of WNV cases increased steadily as the virus spread geographically; in 2003, almost 10,000 cases were reported in the U.S., with 264 deaths. Cumulatively between 1999 and 2010 there have been over 780,000 symptomatic cases of WNV in the U.S. Of these, 16,000 have resulted in neurologic disease, and over 1500 have been fatal. During the 2012 reporting season, the United States reported the second highest number of WNV cases since the outbreak began, with 5674 total cases reported, compared to only 712 cases in 2011. The number of cases per year continues to average greater than 2000 since 2012; however, the location with the most cases varies year to year. Importantly, recent WNV outbreaks have been characterized by an increased number of serious neurological or fatal complications compared to earlier outbreaks. Serious complications from WNV infection are the result of spread of the virus into the central nervous system (CNS), and can result in meningitis, paralysis, and eventually death. Infection of the kidneys has also been reported, although the significance of this and contribution to virus induced morbidity remains unclear. While reasons for the recent increase in severe neurologic cases are unclear, the continued geographic spread and consistent seasonal outbreaks of WNV highlight the need for development of effective vaccines.

WNV (family Flaviviridae, genus *Flavivirus*) is an enveloped positive-strand RNA virus, with a genome that encodes 3 structural and 7 non-structural proteins as a single polypeptide that then co- and post translationally processed to yield the 10 proteins. The 3 virus structural proteins are the capsid (C) protein, pre-membrane protein (prM) which is cleaved during virus maturation to yield the membrane (M) protein and envelope (E) protein. The E protein contains the receptor binding and fusion functions of the virus, and an X-Ray crystal structure for the WNV-E protein, as well as many other members of the genus, have been determined. Like all flavivirus E proteins, the WNV E-protein can be divided into three distinct structural domains; DI, DII, and DIII. Antibodies to domains DII, and DIII have been shown to neutralize the virus, and are correlated with resolution of infection in preclinical models. For this reason, the E-protein has been extensively evaluated as a vaccine candidate in both preclinical animal models. WNV E protein antigen has been delivered as part of an inactivated virus, a recombinant protein, as a DNA vaccine, as an RNA vaccine, and using various replicating and non-replicating viral vectors. Live-attenuated vaccines for WNV have also been developed. Of these, live attenuated vaccines have shown promise in the clinic, inducing high levels of virus neutralizing antibodies. However, due to the potential for persistent viremia in vaccines, these vaccines have important safety concerns, particularly in older or immunocompromised patients who are at high risk for neurologic complications. A recombinant E subunit vaccine, WN-80E, has also been advanced into the clinic, but was found to induce low level neutralizing antibodies when adsorbed to Alhydrogel adjuvant.

Vaccine adjuvants are critical for the effective development of protective responses with many antigens. Toll-like receptor (TLR) agonist adjuvants are particularly promising, as they engage the innate immune system to stimulate a more robust and durable adaptive immune response. Ligands for TLR 7/8 (Imiquimod, Resiquimod), TLR-9 (CpG), TLR-5 (Flagellin), and TLR-4 have been evaluated pre-clinically as components of vaccine adjuvants. TLR-9 and TLR-5 have been specifically evaluated in combination with WNV E protein or domain III antigens, and have shown promise in enhancing immunogenicity in mouse models, However, the safety and scalability of these TLR-agonists may make their use in the clinic problematic. TLR-4 agonist adjuvants, in contrast, have been shown to be safe and effective in several clinical trials, and the TLR-4 agonist adjuvant MPL is a component of the licensed HPV vaccine Cervarix® (GlaxoSmithKline, Rixensart, Belgium).

A need exists for additional WNV vaccines that are safe for use in human subjects while exhibiting increased immunogenicity and durability in order to be sufficiently efficacious.

SUMMARY

The present invention provides a vaccine to protect against disease associated with WNV infection. The vaccine is formed by the combination of a recombinant subunit protein derived from WNV envelope protein and a TLR-4 agonist. The vaccine is capable of inducing a strong and durable immune response. This vaccine formulation utilizes a properly folded recombinant envelope subunit protein ("West Nile 80E" or "WN-80E" or "WN80E" or SEQ ID NO:2) combined with a TLR-4 agonist and a saponin. This vaccine induces relevant, protective immune responses, specifically virus neutralizing antibodies in immunized subjects and is expected to maintain an acceptable safety profile for administration to healthy and immunocompromised individuals.

Accordingly, in one aspect, the present invention provides a West Nile virus vaccine which includes: a) an effective amount of purified West Nile virus envelope ("E") polypeptide, wherein the E polypeptide constitutes approximately 80% of the length of wild type E starting from amino acid residue 1 at its N-terminus; b) an effective amount of a TLR-4 agonist adjuvant; and an effective amount of an saponin adjuvant, wherein the vaccine induces the production of neutralizing antibodies in human subjects. In one embodiment, the TLR-4 agonist is a synthetic lipid A (SLA) derivative, the saponin is a highly purified form of QS21, and the E polypeptide is a polypeptide derived from SEQ ID NO:1. The vaccine may further include a stable oil-in-water emulsion (SE) which may include squalene or a liposome formulation. In one embodiment, the vaccine includes a mixture of SLA and QS21 adjuvants, in a liposomal formulation that is referred to as LSQ.

In another aspect, the present invention provides a method of providing immune protection in a subject against West Nile virus induced disease. The method includes administering an effective amount of the vaccine of the invention to the subject, thereby providing protection from West Nile disease.

In another aspect, the present invention provides a method for raising a protective immune response in a subject. The method includes administering to the subject a therapeutically effective amount of the vaccine of the invention to the subject, thereby raising a protective immune response in the subject.

BRIEF DESCRIPTION OF THE DRAWINGS

FIGS. 3A-3D are graphical representations depicting various data relating to serum antibody titers in embodiments of the invention.

Figures 7A, 7B, 7C, 7D:
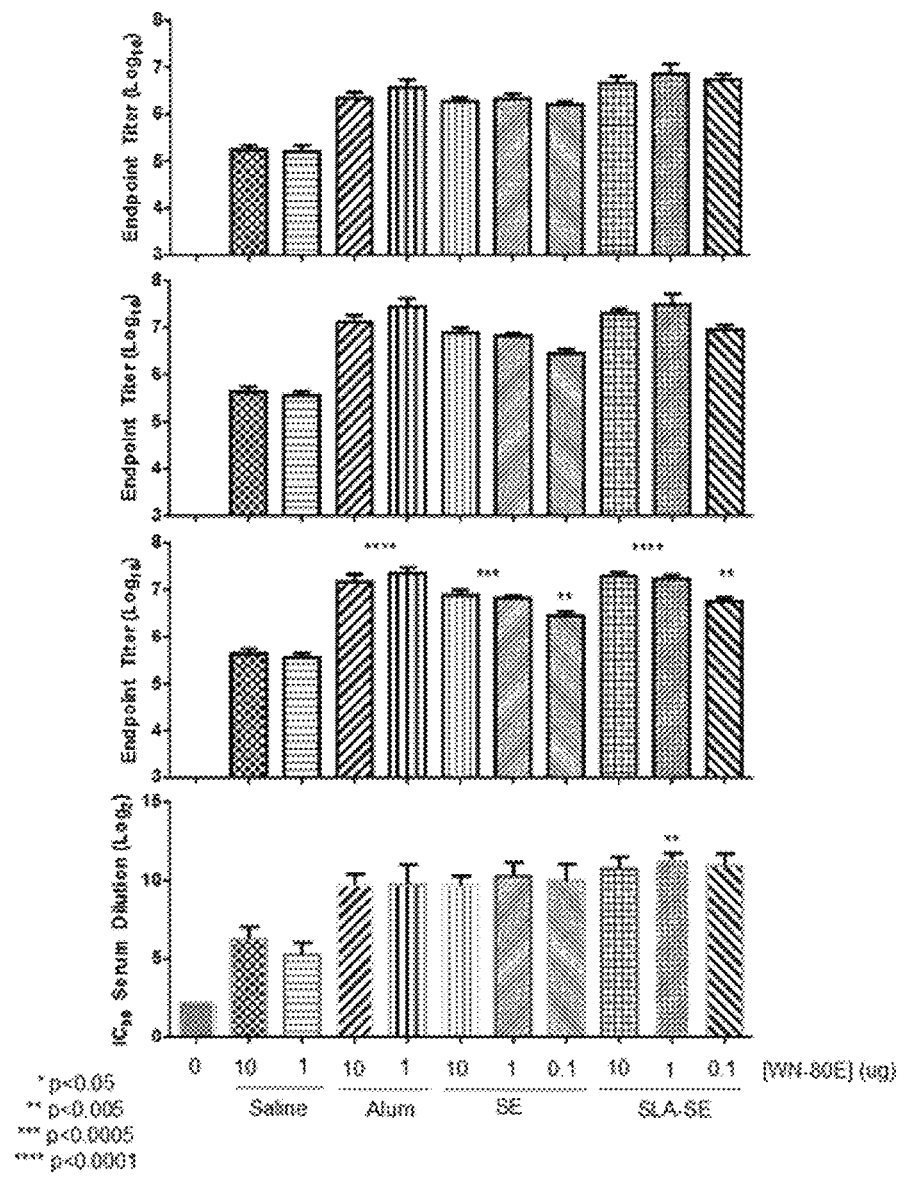

FIGS. 7A-7D are graphical representations depicting various data relating to serum antibody titers in embodiments of the invention.

FIG. 8 is a graphical representation disclosing the amino acid sequence of WN-80E Recombinant Subunit Protein (SEQ ID NO:2). Amino acid numbers are indicated starting at the amino terminus of the protein.

FIG. 9 shows a table of WNV Chimeric PRNT results. The experiments detailed in the following figures identify optimal liposomal formulation containing SLA and QS21 (SLA-LSQ) for rapid and high level induction of protective neutralizing responses to recombinant West Nile Virus antigen (WN-80E). Immunogenicity Study 1: Determine optimal concentration of QS21 for rapid and high level induction of WNV neutralizing antibodies. (ID-C20-100-14). Immunogenicity Study 2: Using fixed QS21 concentration, determine optimal concentration of SLA. (ID-C20-102-14). Immunogenicity Study 3: Determine optimal liposomal composition and investigate the role of antigen encapsulation in induction of immune response (ID-C20-104-14)

Figure 10:
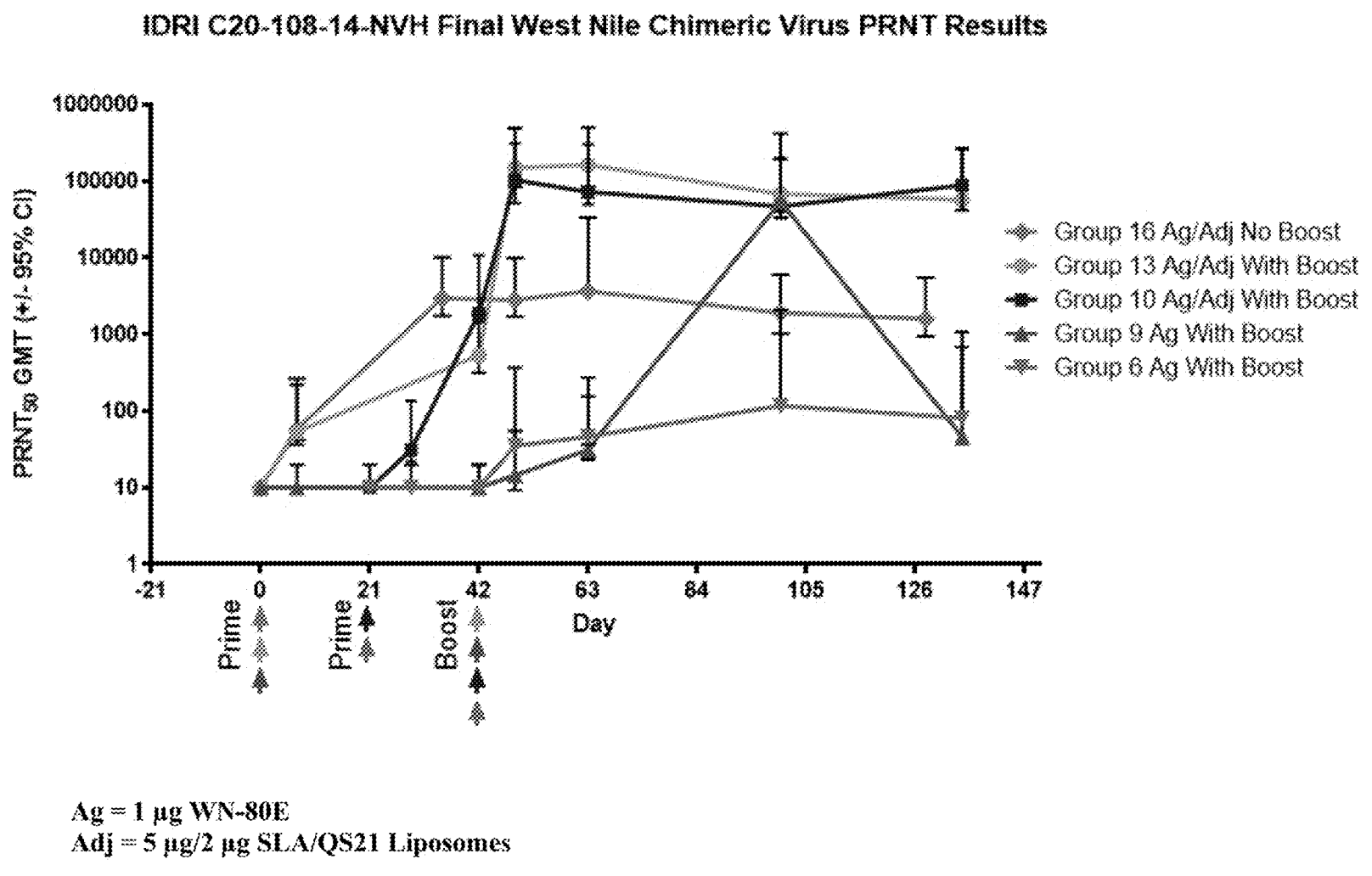

FIG. 10 shows WNV Chimeric PRNT Results in 5 groups of subjects.

FIGS. 13A-13F show induction of germinal centers correlate with increased WN-80E Specific Serum IgG and PRNT titers.

FIGS. 15A-15C show PRNT titers following vaccination with WN-80E+QS21/SLA liposomes.

FIGS. 25A and 25B is a table showing results from a Hamster Challenge.

FIG. 26 shows the results from the study on C20-118-15-NVH WN Chimeric Virus.

FIGS. 28A-28B show SLA-LSQ reduces viral replication in serum to undetectable levels in a Hamster model of WNV Disease following two Immunizations.

FIGS. 29A-29B show SLA-LSQ reduces viral replication in serum to undetectable levels in a Hamster model of WNV Disease following a single Immunization.

DETAILED DESCRIPTION

Figure 1A:
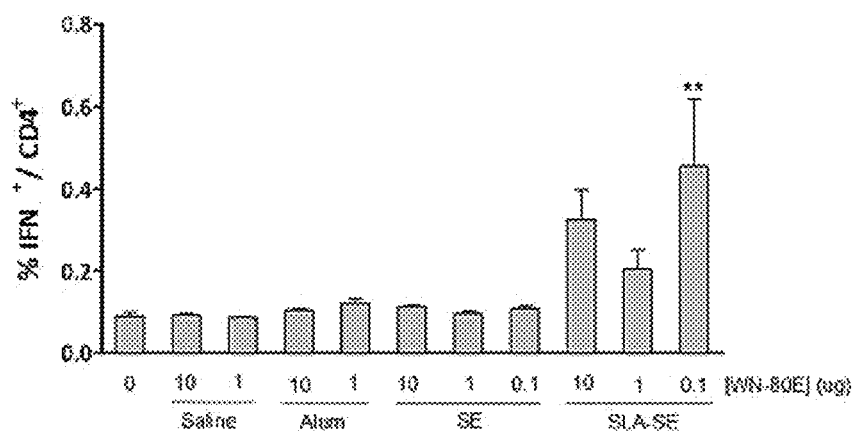
FIGS. 1A-1B are graphical representations depicting various data relating to immunized animals in embodiments of the invention.

The present invention provides a vaccine to protect against disease associated with WNV infection that includes a combination of a recombinant subunit protein derived from WNV envelope protein and a combination of TLR-4 agonist and saponin adjuvants.

Before the present compositions and methods are further described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention is based on the determination that the immunogenicity and protective capacity of a vaccine including a WNV recombinant E-protein (WN-80E) is improved by use with a combination of TLR-4 agonist and saponin adjuvants. Using a model of WNV disease, the present invention is based on the finding that combining a TLR-4 agonist and a saponin adjuvant, a stable oil-in-water emulsion (SE) or liposomes provides both dose and dosage sparing functions and increased durabilty of the immune resposne over time, whereby protection can be induced after a single immunization containing, less than 10 µg of WN-80E. Furthermore, the TLR-4 agaoinst and QS21 adjuvant components can be used a low levels, less than 10 µg each, to induce a potent and durable immune response. Additionally, examination of immunological readouts suggest that induction of a class switched IgG2c antibody response is responsible for the enhance immune responses observed. These findings suggest that inclusion of the appropriate adjuvant combination at low levels greatly enhances the protective capacity of WNV recombinant subunit vaccines, and establish a baseline for future development of these adjuvant combinations.

The WNV vaccine of the present invention utilizes the WN-80E recombinant subunit protein that is produced by means of a cell culture expression system that is based on *Drosophila* Schneider 2 (S2) cells as described in U.S. Pat. App. Pub. No. 20120141520 which is incorporated by reference herein in its entirety. The use of this system results in recombinant envelope subunit proteins that maintain native-like structure. The WNV recombinant envelope protein is truncated at the C-terminus, leaving 80% of the native envelope protein ("80E"). Thus WN-80E is defined as approximately the first 80% of consecutive amino acids of E starting at the first N-terminal amino acid. The C-terminal truncation is designed to delete the membrane anchor portion of the WN E protein (approximately 50 amino acids or 10% from the carboxy terminal end of the full length E protein), in other words, up to the first 90% of consecutive amino acids of WN E protein starting at amino acid 1 of its N-terminus, thus allowing it to be secreted into the extracellular medium and facilitating recovery. More than 90%, but less than 100%, of the E protein can be cloned and secreted, i.e., the protein can be 90%+ in length, carboxy truncated, and can include a portion of the membrane spanning domain so long as the truncated E protein is secretable. "Secretable" means the ability to be secreted, and typically secreted, from the transformed cells of the expression system. The 80E truncation further deletes the "stem" portion of the WN E protein that links the ectodomain of E with the membrane anchor portion. The stem portion does not contain notable antigenic epitopes and therefore is not included.

In one embodiment, the antigen for inclusion in the WNV vaccine is WN-80E. The WN-80E recombinant subunit protein expressed in the *Drosophila* S2 expression system is secreted into the culture medium, is properly glycosylated, and maintains native-like conformation as determined by reactivity with the conformationally sensitive monoclonal antibody 4G2.

The vaccine formulation of the present invention further includes a combination of TLR-4 agonist and saponin adjuvants. The use of this combination of adjuvants with the WN-80E antigen specifically results in a potent and durable immune response that has not been achieved by other adjuvant formulations. Furthermore, this combination of adjuvants allows for the WN-80E vaccine to be administered as a single dose that is capable of producing a protective response.

An ideal TLR-4 agonist is a fully synthetic lipid A molecule (SLA). The most commonly used TLR-4 agonist used for vaccines is monophosphoryl lipid A (MPL). MPL is prepared from bacterial cell walls. The processes used result in heterogeneous preparations of MPL. The synthetic nature of SLA provides for more defined composition relative to MPL. Furthermore, the structure of SLA has been optimized to bind more effectively to the human TLR-4 receptor. SLA enhances the ability of the immune system to respond to vaccine antigens.

An ideal saponin adjuvant is a highly purified preparation derived from the Soap bark tree (*Quillaja saponaria*) and contains a water soluble triterpene glucoside molecule. QS21 is a saponin-based adjuvant of this nature. QS21 is purified from extracts of the tree bark. QS21 enhances the ability of the immune system to respond to vaccine antigens.

In one embodiment, liposomes are combined with the SLA and QS21 adjuvants to form a liposome based formulation. The liposome formulation containing SLA and QS21 is referred to as LSQ. The liposome composition can be either anionic or cationic nature, or more preferably it has a neutral charge. The liposome size range can vary from 20-300 nm, more preferably from 40-200 nm, and most preferably 50-150 nm in size.

In another embodiment, a stable oil-in-water emulsion (SE) which preferably includes squalene is combined with the SLA and QS21 to form a stable oil based emulsion.

The vaccine formulation of the present invention may further include one or more additional pharmaceutically acceptable diluents, carriers, solubilizers, emulsifiers, preservatives and/or adjuvants.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1990).

In an embodiment, the WN-80E protein comprises amino acids 1-401 of WNV, strain NY99. The WN-80E amino acid sequence is provided as FIG. 8 (SEQ ID NO:2). The WN-80E protein is preferably produced from vectors containing an appropriate DNA fragment that encodes the WNV prM protein together with the 80E protein. The encoded prM segment is processed by cellular enzymes in the host cells to release the mature WN-80E protein in a manner that is similar to that which occurs during maturation of the native WNV.

In some embodiments of the invention, WN-80E is defined more broadly as a West Nile virus envelope protein subunit that includes six disulfide bridges at Cys1-Cys2, Cys3-Cys8, Cys4-Cys6, Cys5-Cys7, Cys9-Cys10 and Cys11-Cys12; wherein the polypeptide has been secreted as a recombinant protein from *Drosophila* cells; and wherein the polypeptide generates neutralizing antibody responses to West Nile virus when administered to human subjects.

In an embodiment, the recombinant WNV envelope protein subunit further comprises the disulfide pattern described and a hydrophilicity profile characteristic of a homologous 80% portion of an envelope protein (80E) starting from the first amino acid at the N-terminus of the native WNV envelope protein. In other words, amino acids can be substituted in the sequence comprising WN-80E so long as the disulfide and hydrophilicity profile is maintained to ensure that the recombinant subunit protein retains a native-like structure and appropriate immunogenicity (ability to elicit virus neutralizing antibodies).

Administration and Use

The presently described vaccine provides a method of providing immune protection in a subject against WNV induced disease. The method includes administering an effective amount of the vaccine of the invention to the subject, thereby providing protection from WND. As such, the presently described vaccine provides a means for preventing or attenuating disease that result from infection by WNV. As used herein, a vaccine is said to prevent or attenuate a disease if administration of the vaccine to an individual results either in the total or partial immunity of the individual to the disease, or in the total or partial attenuation (i.e., suppression) of symptoms or conditions associated with the disease.

The term "subject" as used herein refers to any individual or patient to which the subject methods are performed. Generally, the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient. In the present invention the detectable change in the recipient patient is the induction of a neutralizing antibody against WNV.

The vaccine of the invention can be used alone or in combination with other active vaccines such as those containing other active subunits to the extent that they become available. Corresponding or different subunits from one or several viruses or serotypes may be included in a particular formulation. The active vaccine of the invention may further comprise a pharmaceutically acceptable excipient.

The therapeutic compositions of the described invention can be administered parenterally by subcutaneous, intramuscular, or intradermal injection; however, other systemic modes of administration may also be employed. The preferred method of administration for the present invention is the intramuscular route.

Many different techniques exist for the timing of the immunizations when a multiple administration regimen is utilized. Generally, it is preferable to use a vaccine more than once to increase the levels and diversities of expression of the immunoglobulin repertoire expressed by the immunized subject. Typically, if multiple immunizations are given, they will be given one to two months apart. For the vaccine of the invention it is preferable to administer a single dose. To further boost the immune response, a second dose of vaccine can be administered. The preferred immunization schedule for two doses is 0 and 1 months. Other immunizations schedules can also be utilized. For example, alternative immunization schedules such as 0, 2 or 0, 3 months could be used. Additional booster vaccinations may be administered at prescribed intervals such as every 5 to 10 years.

To immunize subjects against WNV-induced disease for example, the vaccine formulation containing the recombinant subunit protein and adjuvant are administered to the subject in conventional immunization protocols involving, usually, multiple administrations of the vaccine. Administration is typically by injection, typically intramuscular or subcutaneous injection; however, other systemic modes of administration may also be employed.

According to the described invention, an "effective amount" of a therapeutic composition is one which is sufficient to achieve a desired biological effect. Generally, the dosage needed to provide an effective amount of the composition will vary depending upon such factors as the subject's age, condition, sex, and extent of disease, if any, and other variables which can be adjusted by one of ordinary skill in the art. The antigenic preparations of the invention can be administered by either single or multiple dosages of an effective amount.

Effective amounts of WN-80E antigen of the invention can vary from 0.01-20 μg per dose, more preferably from 0.5-10 μg per dose, and most preferably 1-5 μg per dose. Effective amounts of the adjuvant components of the invention can vary from about 0.01-20 μg per dose, more preferably from about 0.5-10 μg per dose, and most preferably from about 1-5 μg per dose. The compositions of the invention may further comprise a pharmaceutically acceptable excipient.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

West Nile Virus Vaccine

This example demonstrates the ability of a fully synthetic lipid-A (SLA) TLR-4 agonist to serve as an effective adjuvant when combined with the clinical stage antigen WN-80E (SEQ ID NO:2). It was determined that SLA combined with either a stable oil-in-water emulsion (SE) or combined with Alum can induce a robust WN-80E immune response characterized by production of high level neutralizing antibodies. Furthermore, both of these formulations can affect antigen dose sparing and reduce the viral load in mice to undetectable levels following a single immunization compared to the same formulation without SLA. These results highlight the versatility and utility of SLA as an adjuvant for WNV vaccines, and suggest a vaccine formulation with a well documented safety profile.

Materials and Methods

The following experimental materials and methods were utilized.

Virus Stocks and Vaccines.

Stocks of WNV (NY99 strain) were prepared from infected Vero cells (CCL-81, ATCC). Briefly, Confluent cells were inoculated with WNV at a MOI of 0.1. Virus growth medium (MEM supplemented with 5% fetal bovine serum) was added to the flask after the virus was adsorbed onto drained monolayers for 60 minutes. Cells were examined daily following infection, and supernatant was harvested when cytopathic effect was evident throughout the culture. Decanted medium from the infected cells was clarified by centrifugation at 5000×g for 10 min. Clarified supernatant was supplemented with additional FBS to a concentration of 15%. Virus was aliquoted and stored at −80 C. Thawed stocks were titrated by plaque assay with titers of virus stocks typically $10^8$ pfu/ml.

The WN-80E protein utilized in these studies was provided by Hawaii Biotech, and has been previously described (SEQ ID NO:2; Lieberman et al. (2007) Vaccine 25:414-423; and U.S. Pat. App. Pub. No. 2012/0141520). Briefly, the protein is a carboxy-truncated WNV E-protein which is produced in *Drosophila* S2 cells. Protein was provided in PBS, and stored at −80° C. until use.

Adjuvants and Immunogenicity Studies.

SLA is a synthetic lipid-A derivative which has been previously described. For these studies, SLA was combined with Alhydrogel® (SLA-Alum), combined with a stable oil-in-water emulsion (SLA-SE) containing squalene, or delivered as an aqueous formulation (SLA-AF).

For immunogenicity studies, C57Bl/6 mice were vaccinated via the intra-muscular route in a final volume of 100 μL/immunization (50 μL delivered to each leg) at 0 (prime) and 21 (boost) days. Seven days following each immunization serum, spleen and inguinal lymph nodes were collected for analysis. Twenty one days following each injection, additional serum and bone marrow were collected for analysis of WNV specific antibody titers and for ELISPOT analysis.

Challenge Studies.

Following immunization, C57Bl/6 mice were challenged with $10^5$ pfu of WNV via intra-peritoneal injection of virus in 0.25 mL total volume. Following challenge, all animals were observed daily for signs of virus induced morbidity and mortality. 72 hours following challenge, peripheral blood was obtained from all animals via retro-orbital bleed to determine virus titers.

Plaque Assay.

Serial 10 fold dilutions of serum were prepared in BA-1 medium (M-199 salts, 1.0% bovine serum albumin, 350 mg/L sodium bicarbonate, 100 units/mL penicillin, 100 mg/L streptomycin, and 1.0 mg/L amphotericin in 0.05 M Tris [hydroxymethyl aminomethane], pH 7.6) were prepared in 96 well plates (Corning). Diluted samples were added to 6-well (Corning) plates bearing confluent Vero cells, and incubated for 60 minutes with shaking at 15 minute intervals to ensure even virus distribution. Wells were overlaid with a 0.5% agarose solution and incubated at 37° C. for 48 hours to allow plaque formation. Plaques were visualized by a second agar overlay containing 0.005% neutral red.

Plaque Reduction Neutralization Test (PRNT).

Sera from immunized mice were inactivated by incubation at 56° C. for 30 minutes. Inactivated sera was serially diluted 2-fold in BA-1 medium in a 96 well plate (Corning) beginning with a 1:2.5 dilution in a total volume of 100 μL. Following serum dilution, 100 μL of virus (200 pfu) was added to all serum samples. Virus-serum mixtures were incubated at 4-5° C. overnight or at 37° C. for 60 minutes. Following incubation, virus in all samples was titrated using standard plaque assay techniques. Briefly, virus-serum mixtures were incubated with Vero cell monolayers (200 μL/well) at 37° C. for 45 minutes with rocking to distribute the medium every 15 minutes. Wells were overlaid with 0.5% agarose and incubated for 2 days at 37° C. in a $CO_2$ incubator, followed by second overlay with additional agar containing 0.005% neutral red. Plaques were enumerated on day 3. Negative (media only) and positive controls (immune serum) were included in each assay.

Antibody Responses.

WN-80E-specific endpoint titers for IgG, IgG1 and IgG2c were determined seven days and twenty-one days post immunization. High binding polystyrene 384 well plates were coated with WN-80E (2 μg/ml) in 0.1 M bicarbonate coating buffer for 2.5 hours at room temperature. Plates were washed three times with 0.1% PBS-Tween 20 pre and post a two hour blocking incubation with 0.05% PBS-Tween 20+1% BSA at room temperature. Mouse sera was serially diluted in 0.05% PBS-Tween 20+0.1% BSA using the Nanonscreen™ NSX-1536 and incubated overnight at 4° C. and washed five times. Plates were incubated for 1 hour on the shaker with anti-mouse IgGT, IgG1 or IgG2c HRP conjugates (Southern Biotechnologies). Following five washes, plates were developed on the Nanoscreen™ robot using SureBlue™ tetramethylbenzidine substrate (Kirkegaard & Perry Laboratories). The enzymatic reaction was stopped with 1 N $H_2SO_4$ using the Muitipette Sagian™ robot. Plates were read at 450-570 nm using the Synergy ELISA plate reader (Biotek) and Gen5™ software.

Intracellular Cytokine Staining.

In order to quantify vaccine specific T-Cell responses, splenocytes were isolated from five mice per group following immunization. Red blood cells were lysed using Red Blood Cell Lysis Buffer (eBioscience) and resuspended in cRPMI 1640 (10% FBS, 1% Penicillin/Streptomycin; 0.1% 2-Mercaptoethanol). Cells were plated at $10^7$ cells/well in 96-well plates and were stimulated for 2 hours with media or WN-80E Antigen (10 µg/mL) at 37° C. 1:50 GolgiPlug (BD Biosciences) was added and the cells were incubated for an additional 8 hours at 37° C. Cells were washed and surface stained with fluorochrome labeled antibodies at 1:100 in 1% BSA-PBS to CD4 (clone RM4-5), CD8 (clone 53-6. 7), CD44 (clone IM7) and B220 (RA3-6B2) (BioLegend and eBioscience) in the presence of anti-CD16/32 (clone 93) for 15 minutes in the dark at room temperature. Cells were fixed and permeabilized with Cytofix/Cytoperm™ (BD Biosciences) for 30 minutes at room temperature in the dark. Cells were washed with Perm/Wash™ (BD Biosciences) and stained with fluorochrome labeled antibodies to detect intracellular cytokines as follows: IFN-γ (clone XMG-1.2), IL-2 (JES6-5H4), TNF (MP6-XT22), IL-5 (clone: TRFKS) and IL-10 (clone: DESS-16E3) (BioLegend and eBioscience) Staining was carried out for 15 minutes at room temperature in the dark. Cells were washed, resuspended in 1% BSA-PBS and filtered using a 30-40 um PP/PE 96 filter plate (Pall Corp). Up to $10^6$ events were collected on a four laser LSR Fortessa™ flow cytometer (BD Biosciences). Data were analyzed with FlowJo™ (Treestar). Analysis and presentation of distributions was performed using SPICE version 5.2, downloaded from Hypertext Transfer Protocol exon.niaid.nih.gov/spice.

B CELL Quantification.

Seven days following immunization, inguinal lymph nodes were isolated from five animals per group. Cells were re-suspended in cRPMI 1640 (10% FBS, 1% Penicillin/Streptomycin; 1:1000 2-Mercaptoethanol) and plated at $10^7$ cells/well in 96-well plates. Cells were surface stained in staining buffer {1% FBS, 1:250 EDTA, PBS) with fluorochrome labeled antibodies (1:200) to CD138 (clone281-2), GL7 (clone GL7), CD95 (clone Jo2), IgM (clone II/41), CD19 (clone 1D3 or 6D5), IgD (clone 11-26c.2a), CD38 (clone 90) and 1:100 CD16/32 (clone 93) for 15 minutes in the dark at 4° C. Non B cell lineage cells were excluded by staining (1:200) and gating for LysG (clone 1A8), CD11b (clone M1/70), CD11c (clone N418), F4/80 (clone BM8), Ter119 (clone TER-119) and Thy1.2 (clone 53-2.1) hi populations. Cells were fixed and permeabilized with Cytofix™/Cytoperm™ (BD Biosciences) for 20 minutes at room temperature in the dark and washed with Perm/Wash (BD Biosciences). IgG subtype staining was carried out for IgG1 (clone RMG1-1) and biotinylated-IgG2a,b,c (clone 5.7). IgG2a,b,c was detected by addition of streptavidin (1:500) for 15 minutes at 4° C. in the dark. Cells were resuspended and filtered in staining buffer using a 30-40 µm PP/PE 96 filter plate (Pall Corp). Up to $10^6$ events were collected on a four laser LSR Fortessa™ flow cytometer (BD Biosciences). Data were analyzed with FlowJo™ (Treestar). Analysis and presentation of distributions was performed using SPICE version 5.2, downloaded from Hypertext Transfer Protocol exon.niaid.nih.gov/spice.

Description of Relevant Figures

Figure 1B:
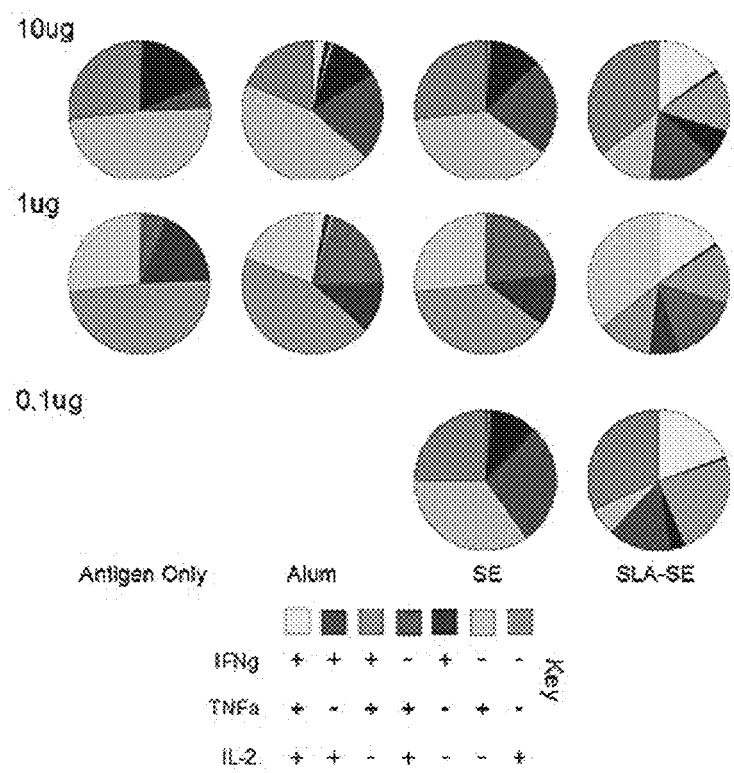

FIGS. 1A-1B are graphical representations of data showing induction of a Th1 CD4+ T-Cell response in SLA-SE immunized animals. Seven days following immunization, isolated splenocytes were phenotyped by ICS. IFNγ+ CD4 T-cells were induced following immunization with WN-80E in combination with SLA-SE. At decreased antigen doses (100 ng/mouse), inclusion of GLA-SE resulted in a significant increase in cytokine positive cells relative to antigen only controls (p<0.005)(A). Additional cytokine profiling shows that many of the IFNγ cells in the SLA-SE group displayed a Th1 phenotype, and were positive for TNFα and/or IL-2 (B).

FIGS. 2A-2D are graphical representations related to ELISA titers following a single immunization with WN-80E. Serum antibody titers were determined by ELISA 21 days following a single immunization with WN-80E in combination with adjuvants. Titers of Total IgG (A), IgG1 (B) and IgG2c (C) were determined for all mice (n=5/group). Similar levels of Total IgG and IgG1 were observed in all immunized animals. Significantly elevated levels of IgG2c were detected in mice immunized with SLA-SE compared to those immunized with 10 µg of antigen alone (p<0.0001). Neutralizing antibody titers were also determined by PRNT assay (D) to assess antibody function. There is a trend toward increased titer in SLA-SE immunized animals.

FIGS. 3A-3D are graphical representations of data showing that SLA formulated with Alum or SE increases functional antibody titer following a single immunization with WN-80E. Serum antibody titers were determined by ELISA 21 days following a single dose of WN-80E in combination with Alum or SE formulations with or without SLA. Anti-WN-80E titers of Total IgG (A), IgG1 (B) and IgG2c (C) were determined for all mice (n=5/group). Compared with animals immunized with 10 µg of WN-80E, animals immunized with 1 µg showed significantly reduced titers for all antibody subtypes. Significantly elevated levels of IgG2c were detected in mice immunized with SLA-SE compared to those immunized with 10 µg of antigen alone (P<0.0001). Neutralizing antibody titers were also determined by PRNT (D) to assess antibody function. There is a trend toward increased titer in animals immunized with either SLA-Alum or SLA-SE, and an inverse relationship between antigen dose and PRNT titer.

Figure 4A:
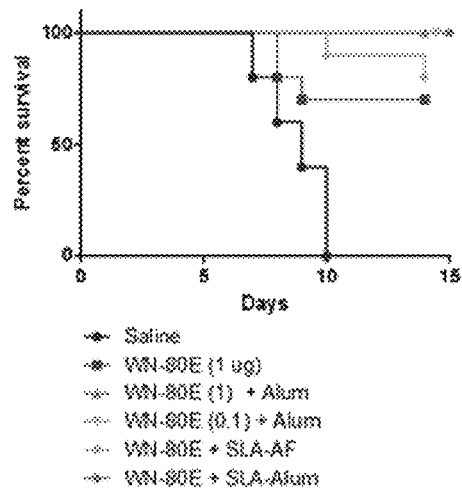
FIGS. 4A-4C are graphical representations depicting various data relating to immunized animals in embodiments of the invention.
Figure 4B:
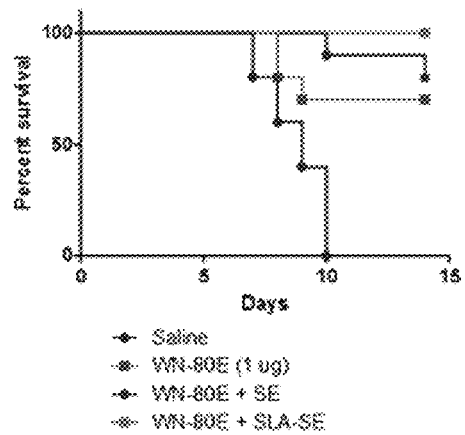
Figure 4C:
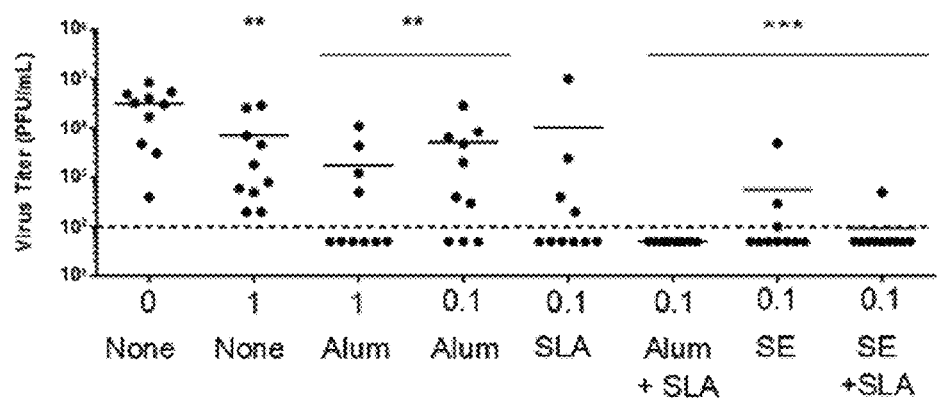

FIGS. 4A-4C are graphical representations of data showing that immunization with SLA containing adjuvants in combination with WN-80E enhances survival and reduces viral titer to undetectable levels. Following a single vaccination of WN-80E in combination with the indicated adjuvants, mice (n=10/group) were challenged with XX LD50 of WNV via the intraperitoneal route. Survival of mice was monitored over 14 days following challenge (A,B). Three days post-challenge, serum was collected from all animals in order to assess virus titers. Animals immunized with SLA-Alum had undetectable titers in all animals (P<0.0005). Those immunized with SE or SLA-SE had minimal titers while those immunized with Alum, SLA-AF or no adjuvant showed only slightly reduced titers compared to unimmunized controls (P<0.005).

FIG. 5 is a series of graphical representations of data showing that immunization with protective adjuvants induces an increase number of germinal center B-Cells expressing IgG2c antibodies. Animals were immunized twice with WN-80E in combination with Alum or Stable Emulsions with or without SLA. Seven Days following each immunization, inguinal lymph nodes were removed and stained for by ICS for B cell markers. SLA containing formulations, particularly when combined with Alum or SE, induced increased numbers of preplasmablast b-cells (lineage-/CD19lo/CD138+) following both prime and boost injections (A). SLA containing adjuvants as well as SE alone stimulated an increased number of germinal center (lineage-/CD19+/CD95+GL7+) cells (GC) following immunization (B).

Figure 6A:
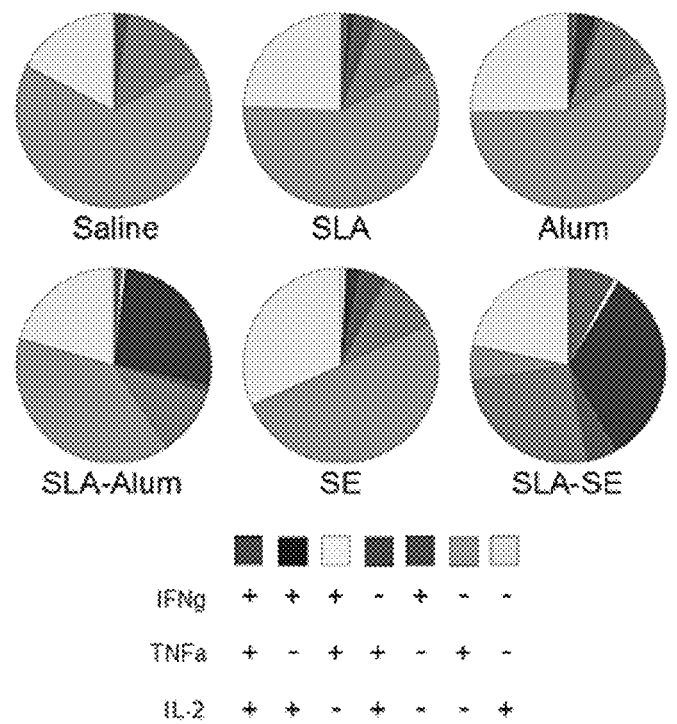
FIGS. 6A-6B are graphical representations depicting various data relating to immunized animals in embodiments of the invention.
Figure 6B:
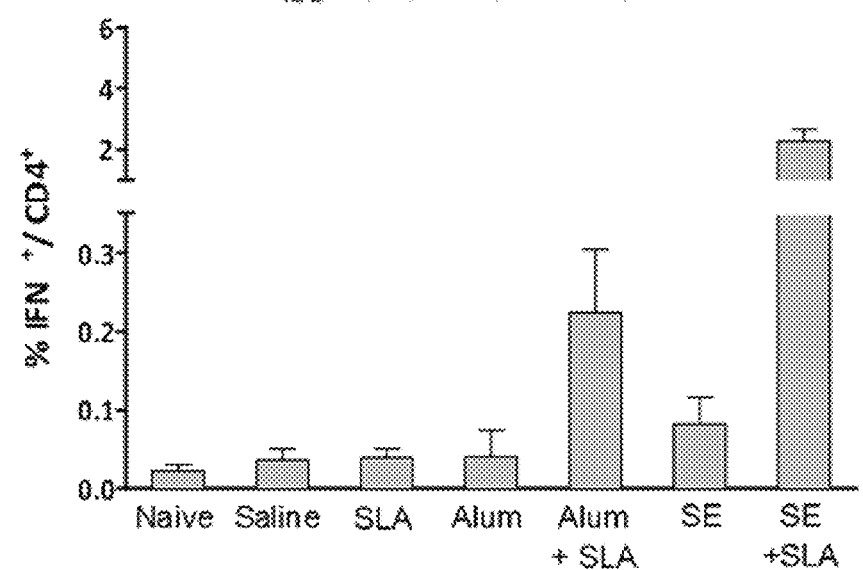
Figure 11:
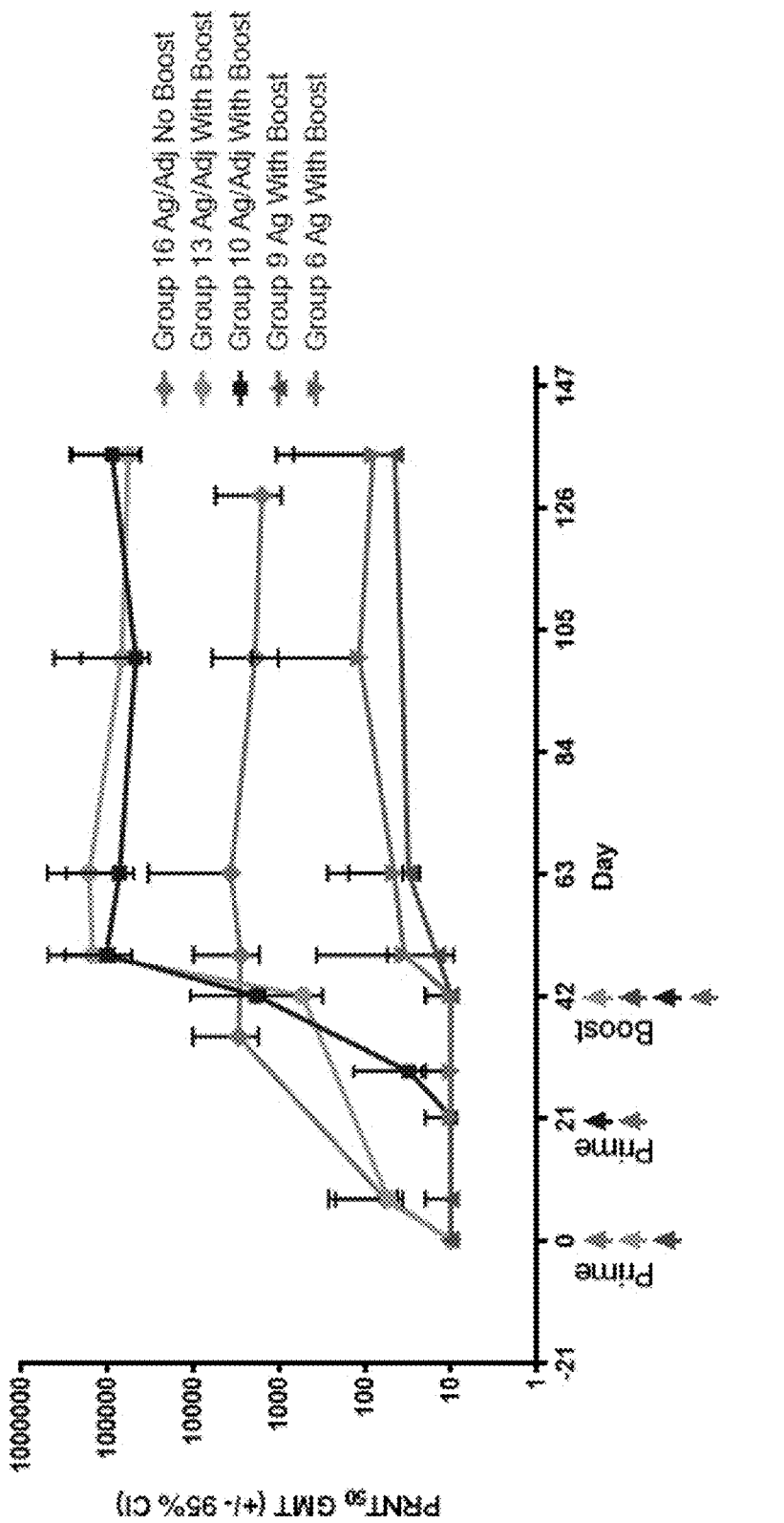
FIG. 11 shows WNV Chimeric PRNT Results in 5 groups of subjects.
Figure 12:
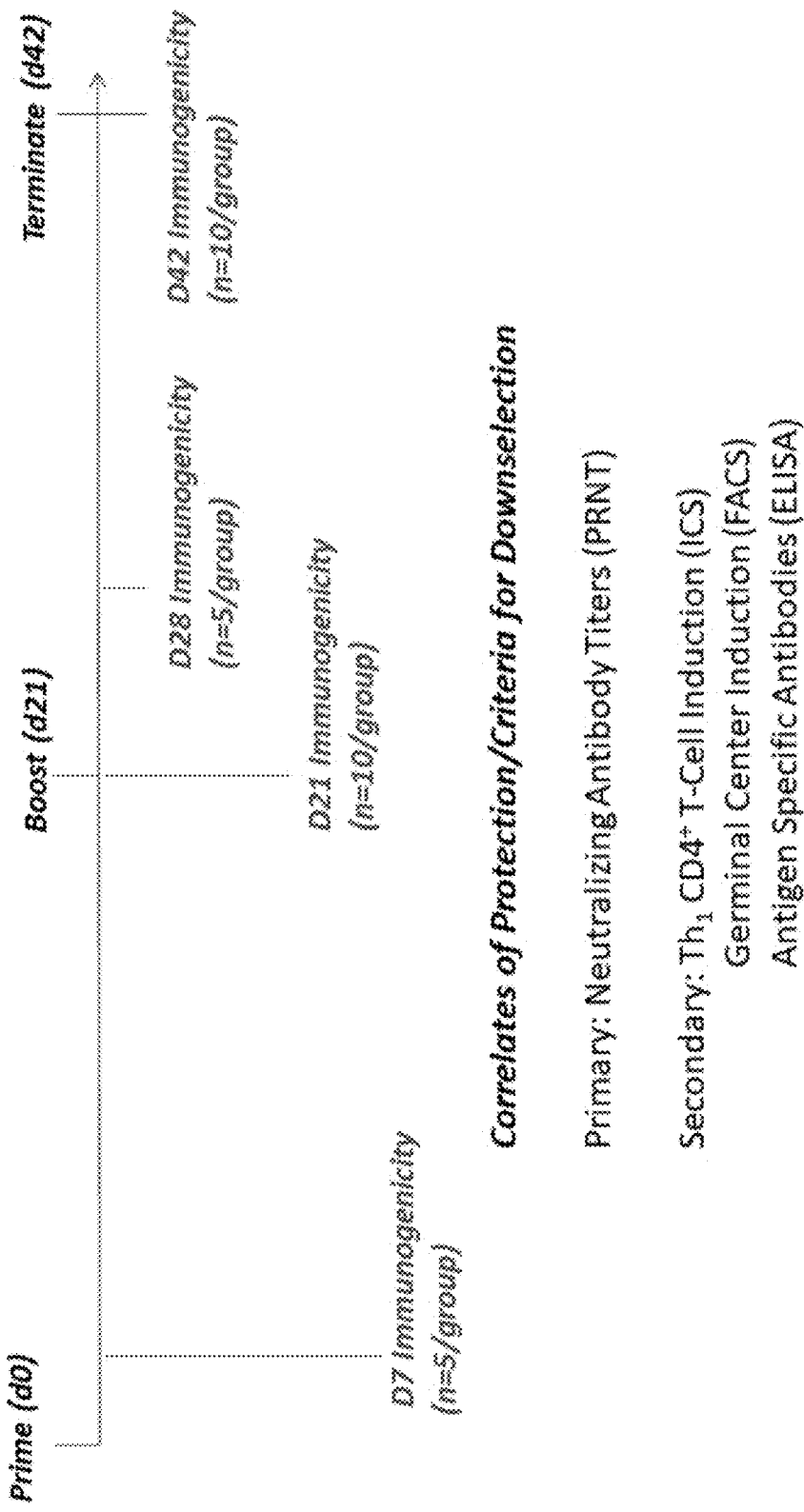
FIG. 12 shows the Experimental design for WNV vaccination.
Figure 14:
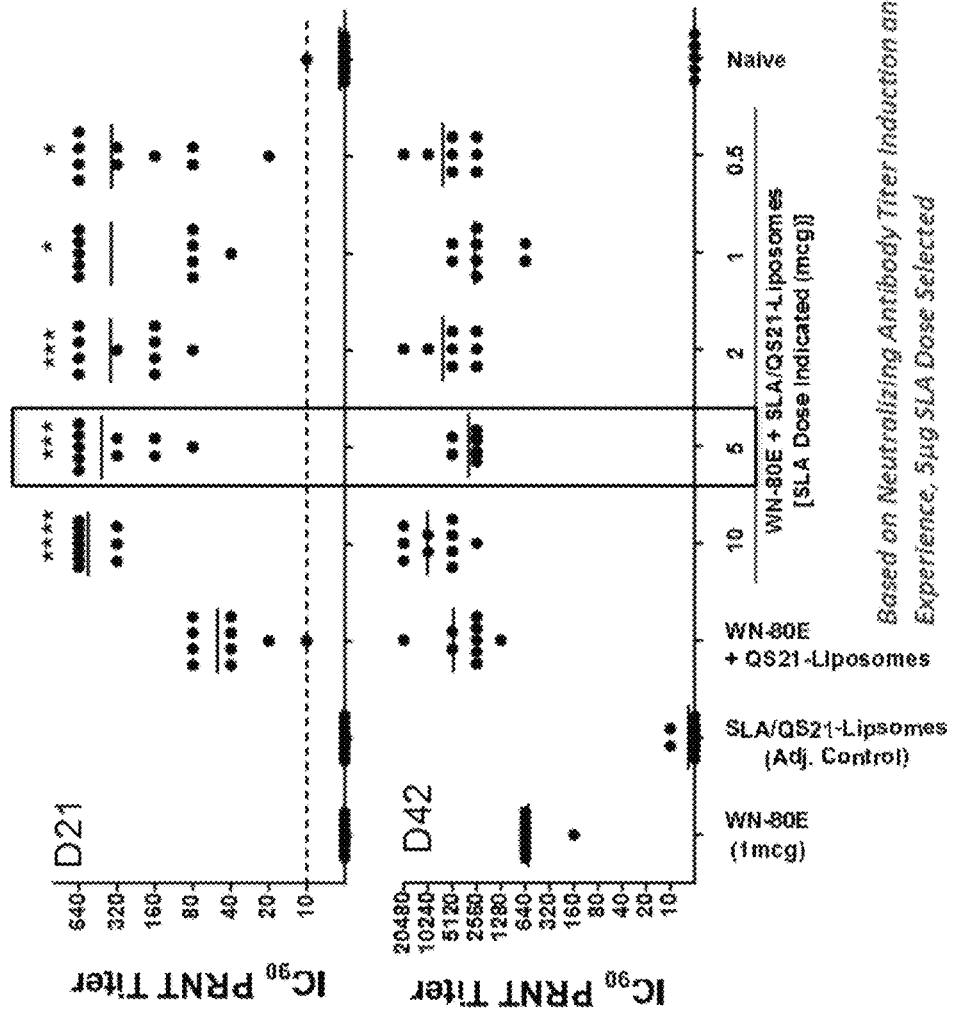
FIG. 14 shows PRNT results-inclusion of SLA results in a statistically significant increases in neutralization titer.
Figure 16:
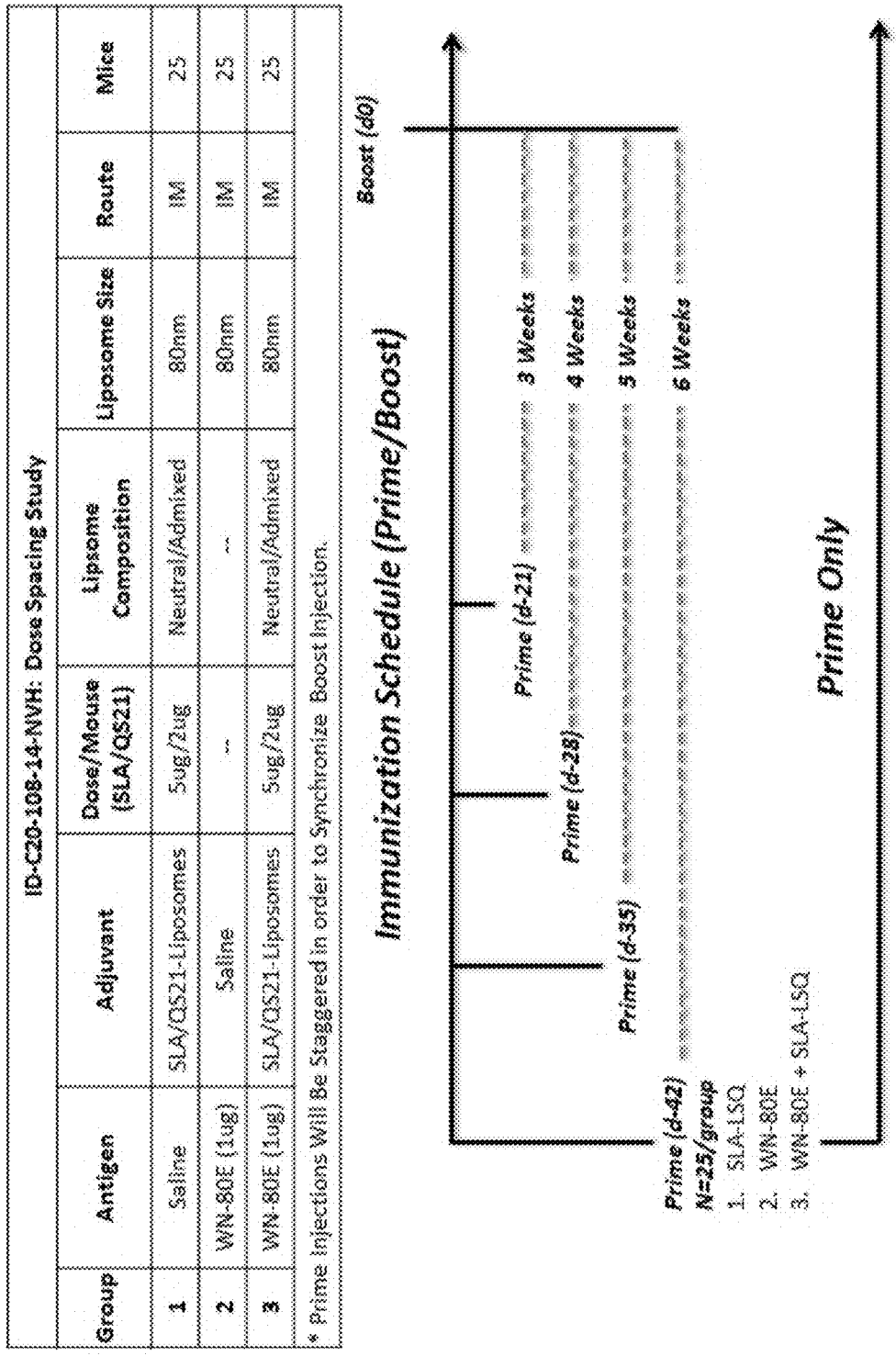
FIG. 16 shows the experimental design for ID-C20-108 and immunization schedule.
Figure 17:
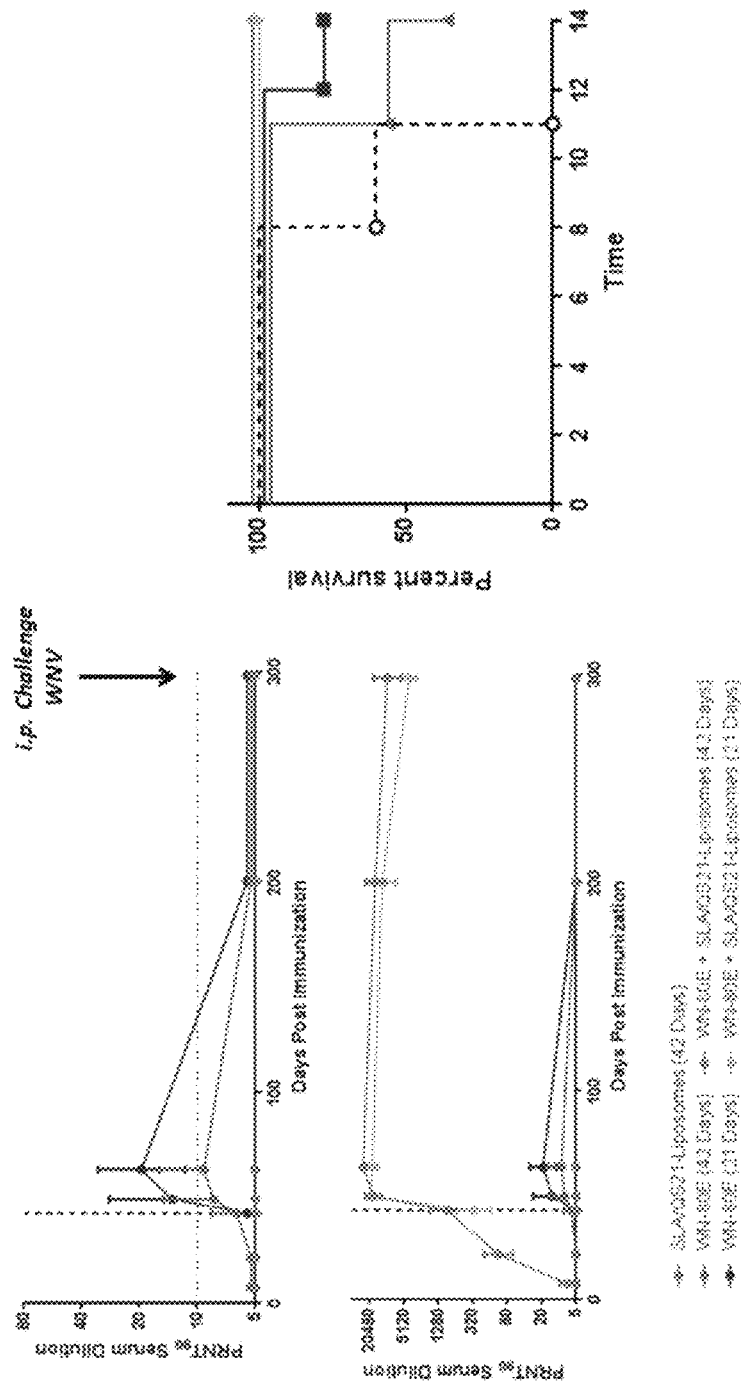
FIG. 17 shows ID-C20-108-14: Long Lived Neutralizing Antibody Responses Following Prime-Boost Immunization with WN-80E+SLA-LSQ.
Figure 18:
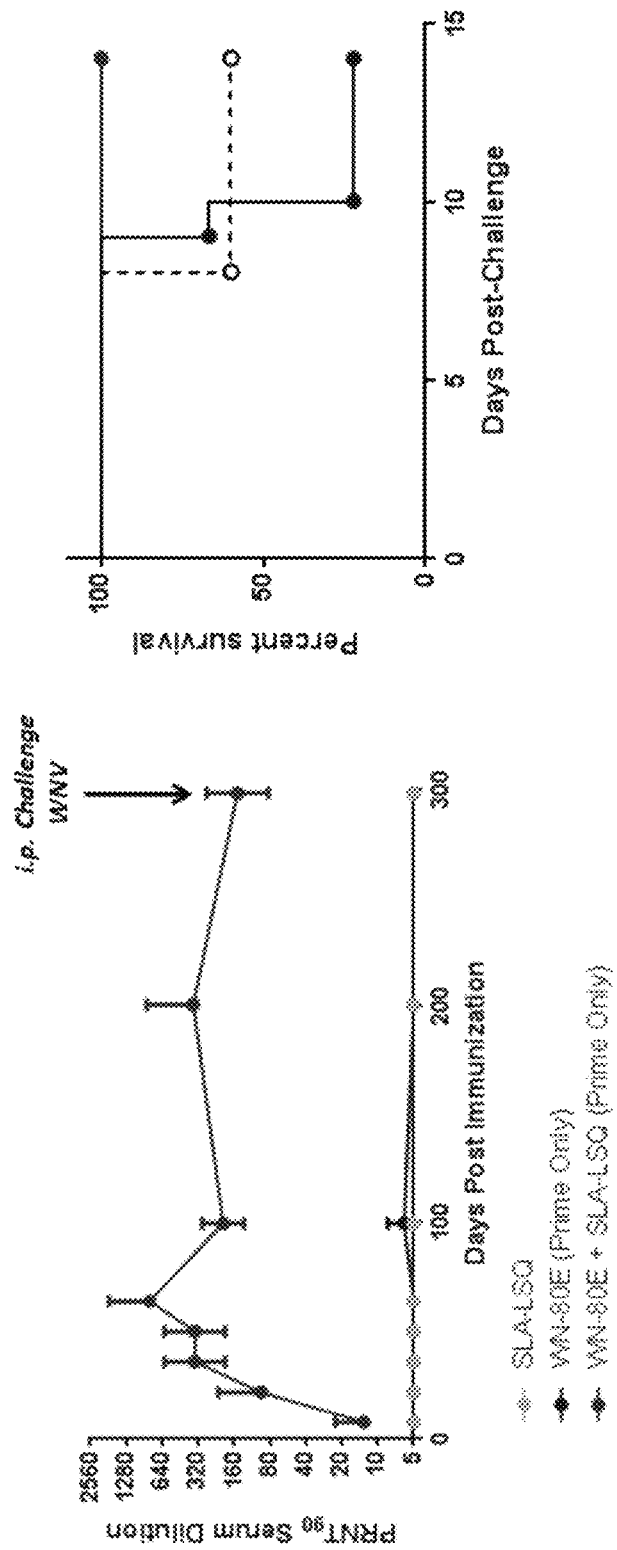
FIG. 18 shows a Single Immunization with WN-80E+SLA-LSQ is Protective Over 300 Days Post-Immunization.
Figure 19:
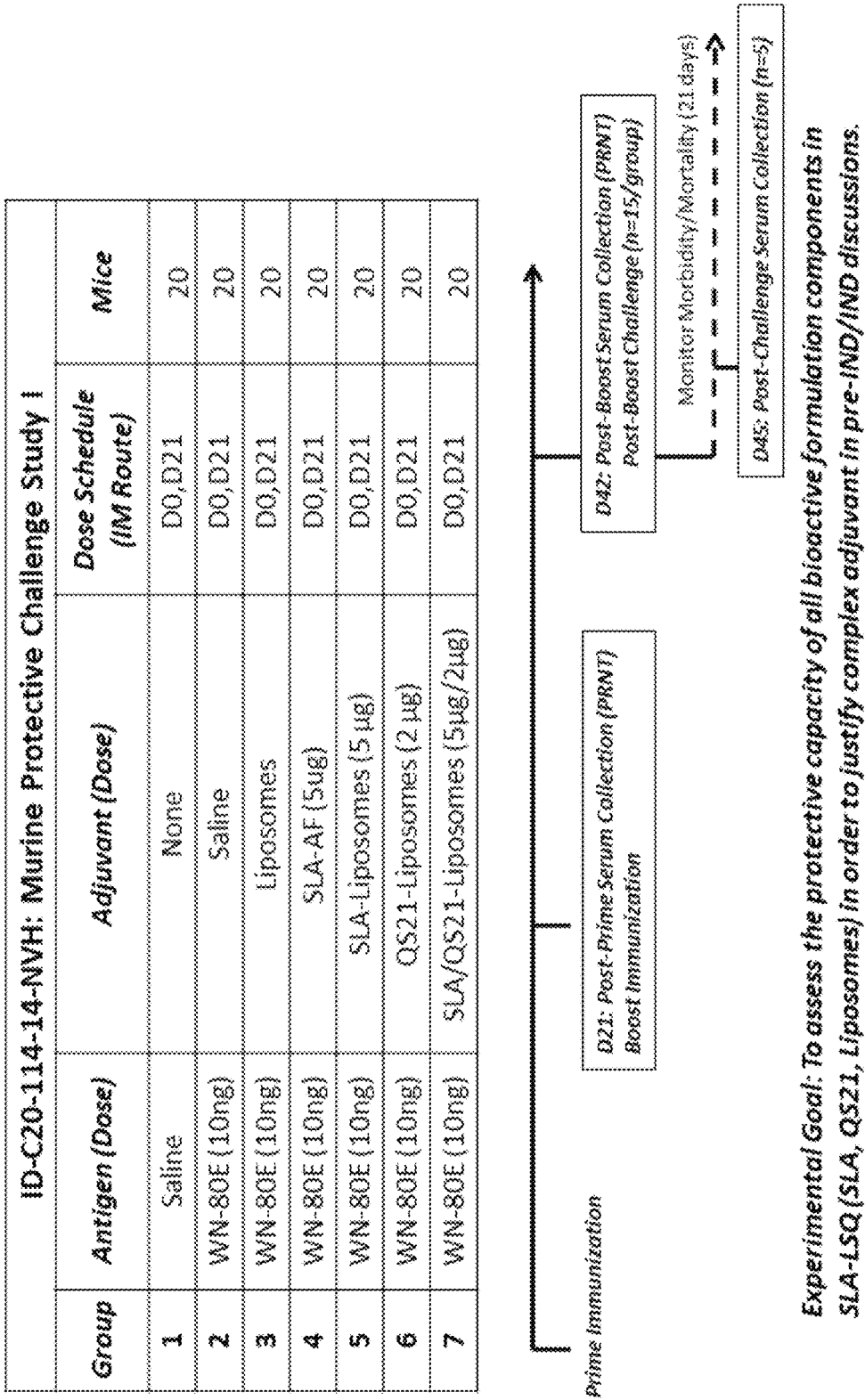
FIG. 19 shows experimental design for ID-C20-114-14-NVH.
Figure 20:
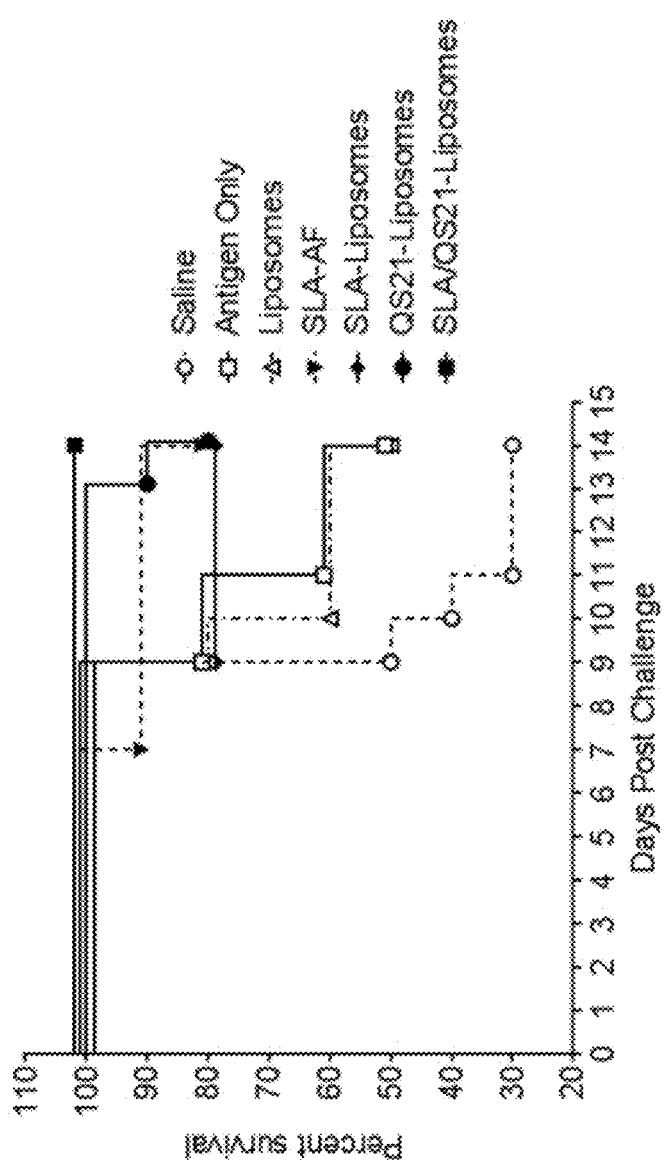
FIG. 20 shows survival following Prime-Boost Immunization with Low Dose WN-80E+SLA Adjuvants (ID-C20-114-15).
Figure 21:
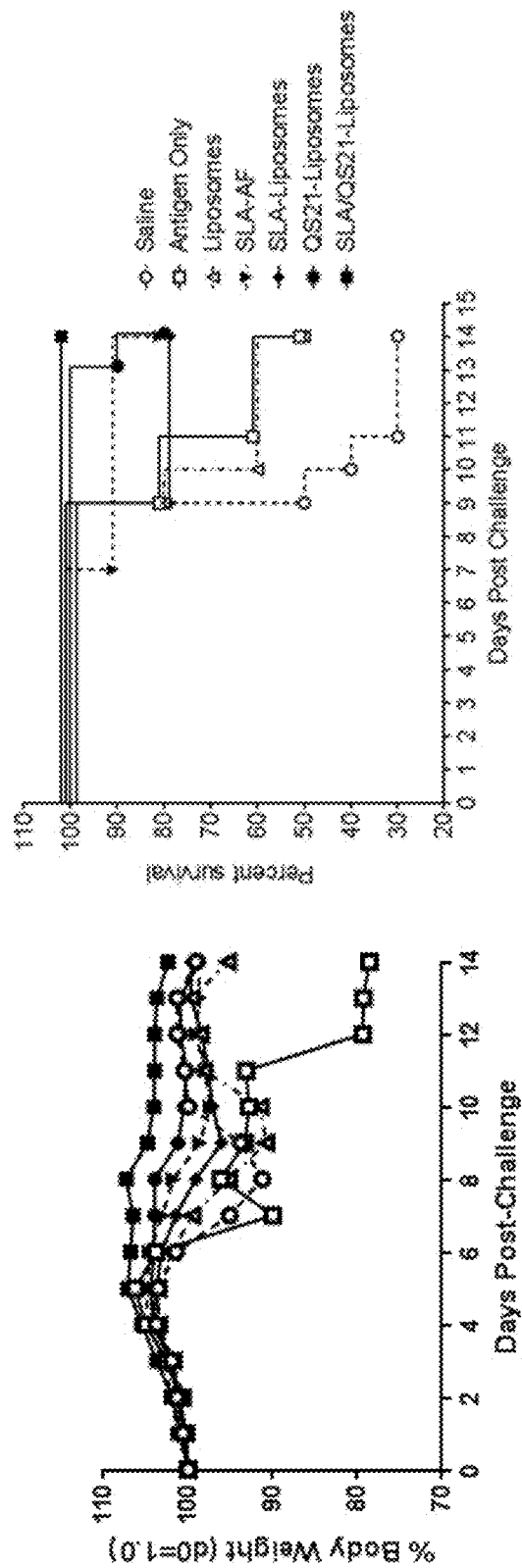
FIG. 21 shows survival following Prime-Boost Immunization with Low Dose WN-80E+SLA Adjuvants (ID-C20-114-15).
Figure 22:
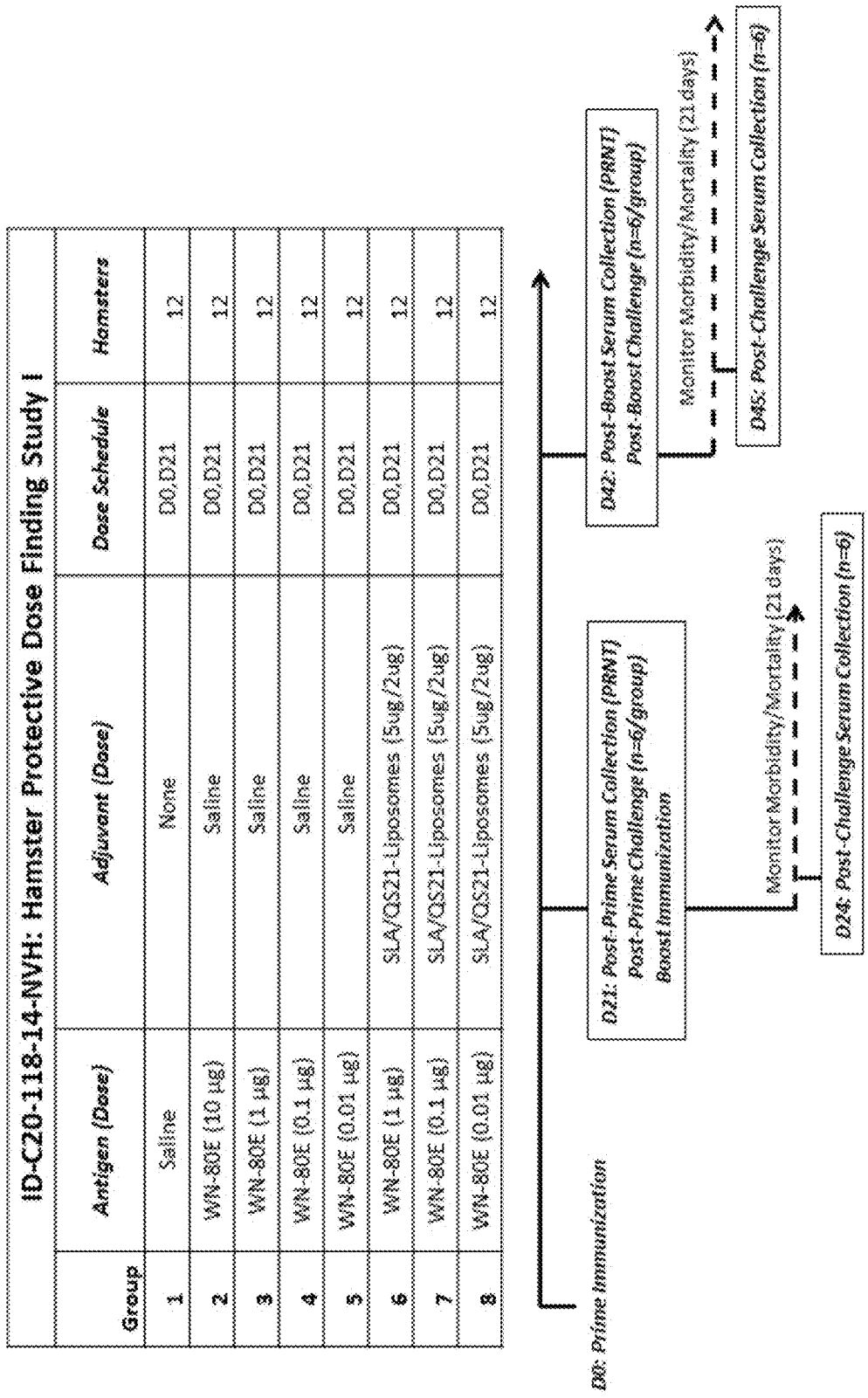
FIG. 22 shows experimental design for ID-CD20-118.
Figures 23A, 23B:
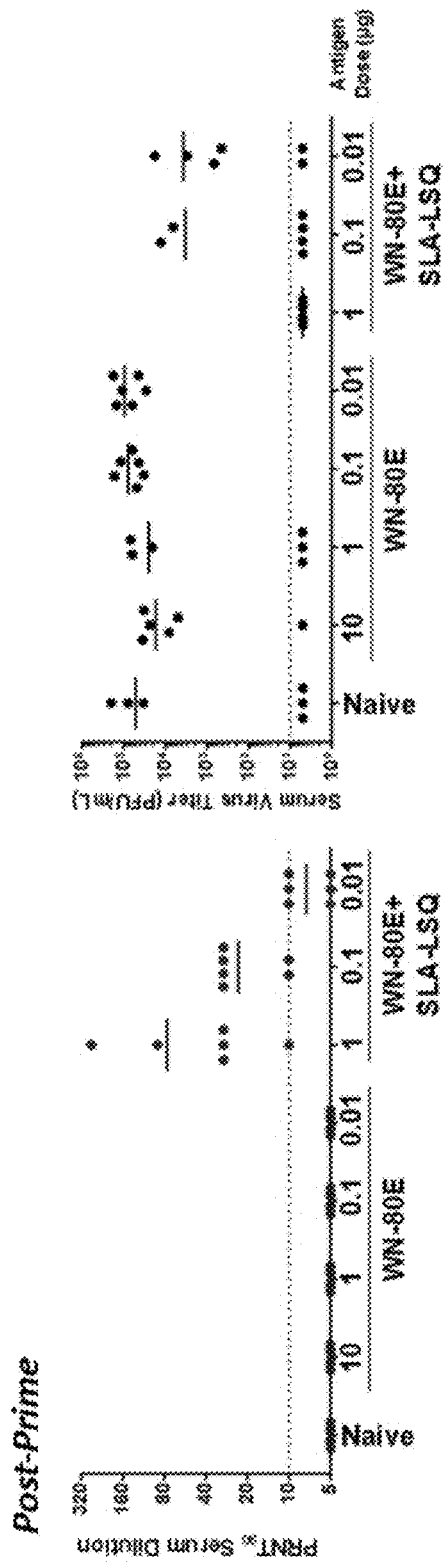
FIGS. 23A-23B show post-prime PRNT and serum virus titer following immunization in Syrian Golden Hamsters.
Figure 24A:
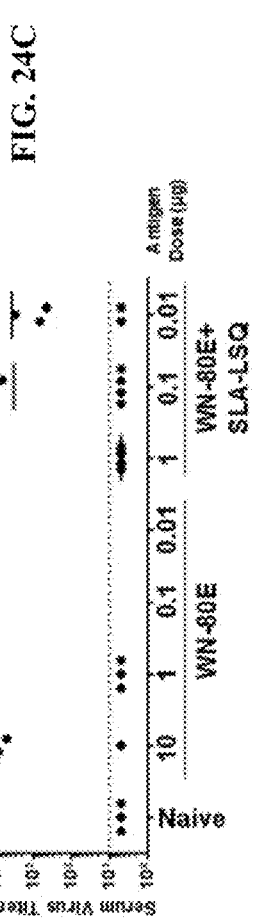
FIG. 24A-24D shows PRNT and serum virus titer following immunization in Syrian Golden Hamsters.
Figure 24B:
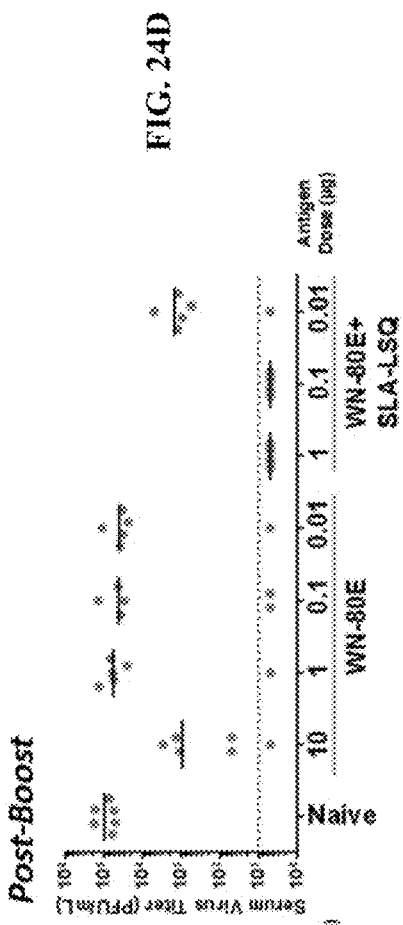
Figure 24C:
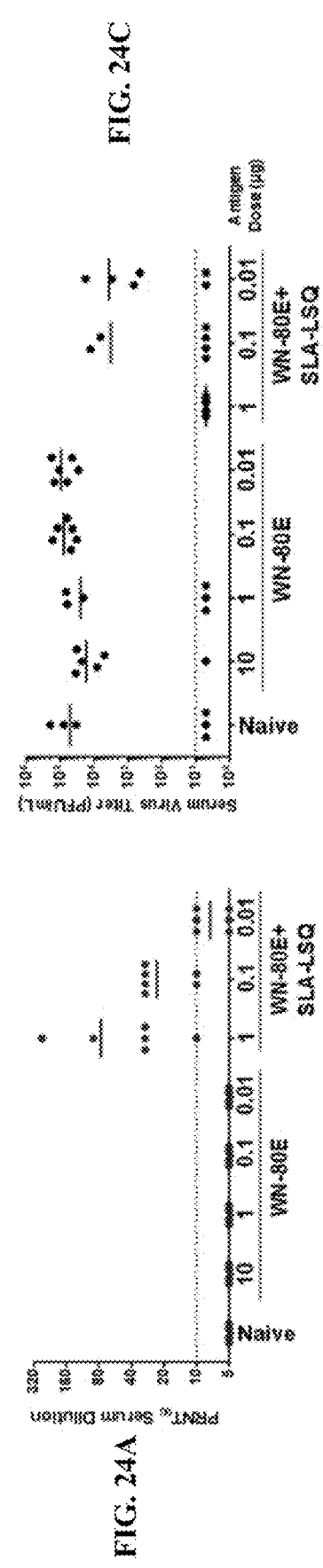
Figure 24D:
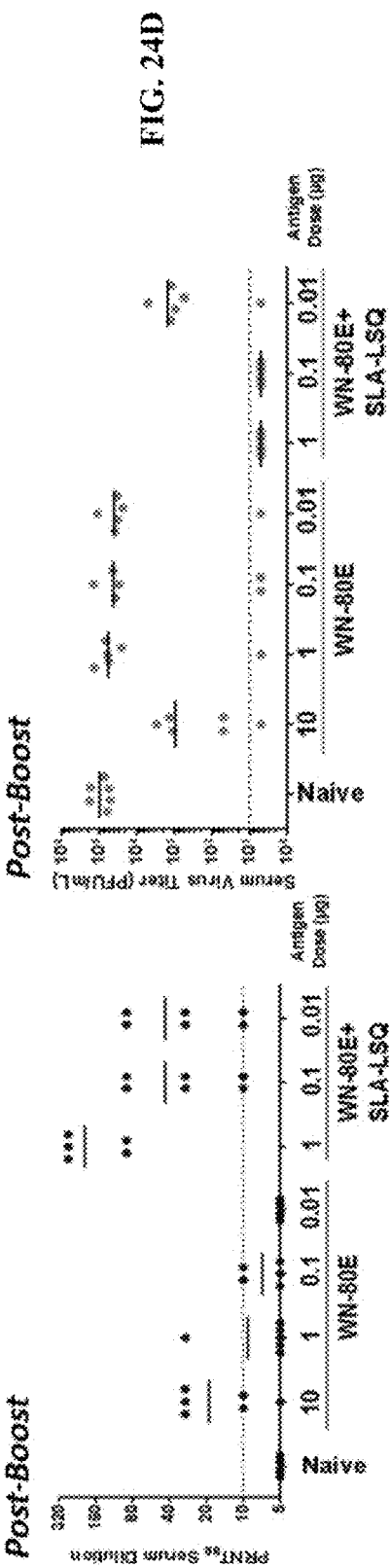
Figure 27:
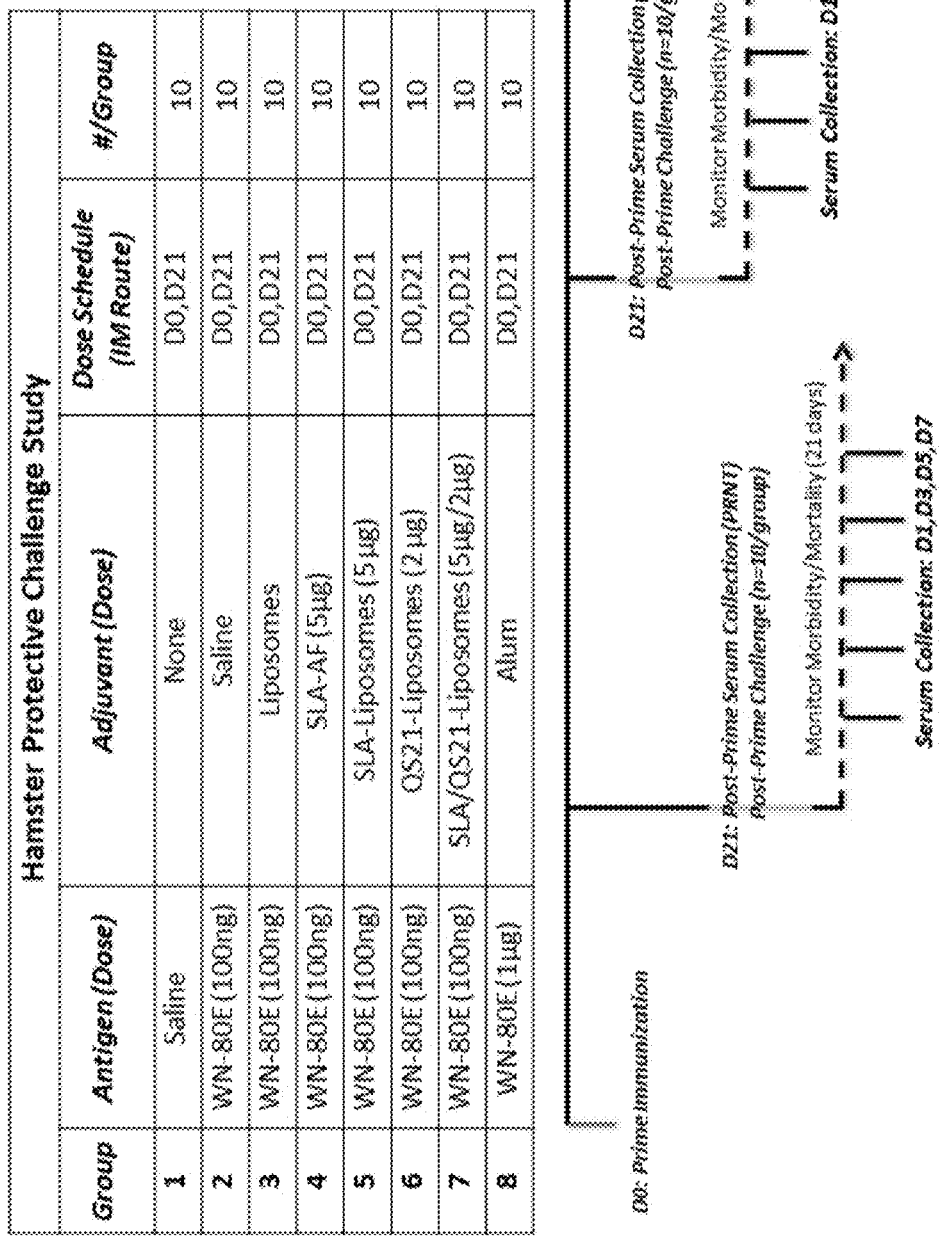
FIG. 27 shows the Hamster challenge study design.

FIGS. 6A-6B are graphical representations of data showing that protective adjuvants induce a robust Th1 CD4+ T-cell response following a single immunization. Mice (n=5/group) were immunized with WN-80E (1 µg/dose) in combination with the indicated adjuvants. 7 days following a single immunization, splenocytes were isolated and phenotyped by ICS. The SLA containing adjuvants shown to be most protective in challenge studies induced an increased number of CD4+ T-cells with a Th1 phenotype. Increased numbers of IFNg+ cells were observed (A), and many of these were also positive for other Th1 cytokines including TNFa and IL-2 (B).

FIGS. 7A-7D are graphical representations of data showing induction of WN-80E specific antibodies in serum following two injections with WN-80E. Serum antibody titers were determined by ELISA 21 days following a boost immunization with WN-80E in combination with adjuvants. Titers of Total IgG (A), IgG1 (B) and IgG2c (C) were determined for all mice (n-5/group). Similar levels of Total IgG and IgG1 were observed in all immunized animals. Significantly elevated levels of IgG2c were detected in mice immunized all adjuvants compared to those immunized with 10 µg of antigen alone. Unlike results obtained following a single injection, IgG2c levels were elevated in all animals receiving adjuvant relative to those receiving antigen only. Neutralizing antibody titers, determined by PRNT assay (D), were also elevated in all animals receiving adjuvant.

Results

SLA Stimulates Higher WNV Neutralizing Antibody Titers Following a Single Dose in Mice.

Figure 2A:
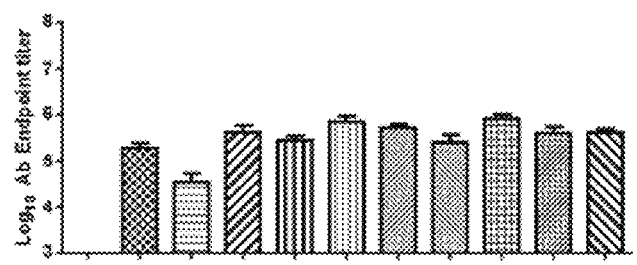
FIGS. 2A-2D are graphical representations depicting various data relating to serum antibody titers in embodiments of the invention.
Figure 2B:
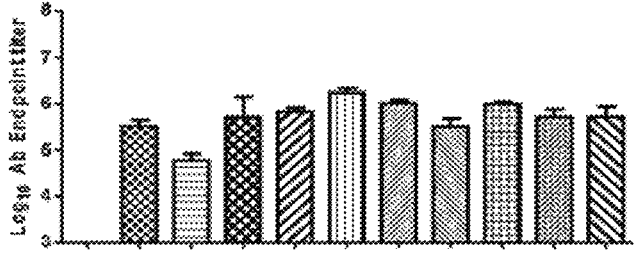
Figure 2C:
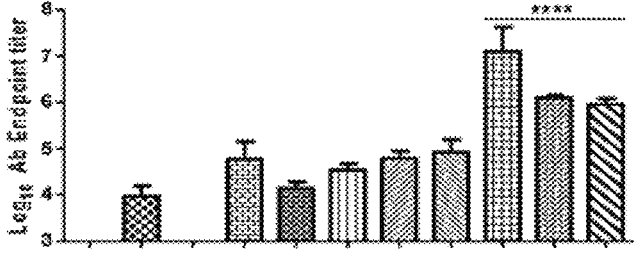
Figure 2D:
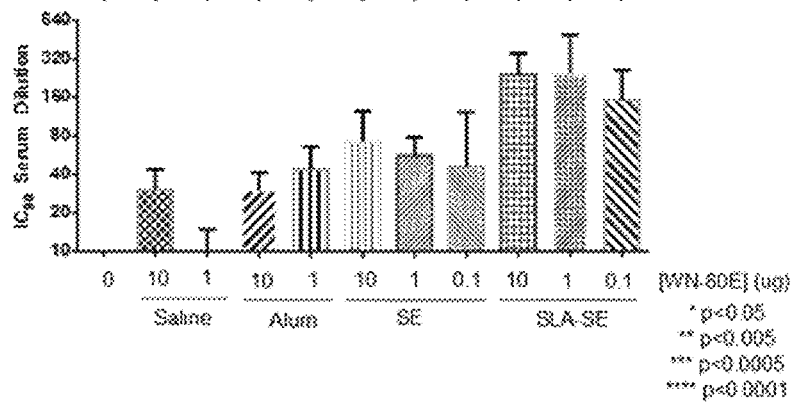

Using the mouse model, the ability of the TLR-4 agonist adjuvant synthetic lipid A (SLA) formulated in a stable oil-in-water emulsion (SE) was evaluated to enhance the immune response and enable antigen dose-sparing when combined with WN-80E. In addition, the inventors sought to compare these adjuvant formulations to WN-80E formulated with alum. Following a single injection of WN-80E adjuvanted with alum, SE or SLA agonist combined with SE (SLA-SE), both the cellular and humoral WN-80E specific immune responses were examined. Seven days following immunization, it was observed that an increase in the number or WN-80E specific IFNγ+ CD4+ cells in the spleen of SLA-SE immunized animals compared to those immunized with SE alone or Alum (FIG. 1A). ICS analysis of T-cell populations demonstrated that many of these IFNγ+ T-cells were polyfunctional, with a high percentage those from the SLA-SE immunized animals showing a canonical Th1 phenotype (IFNγ+/TNFα+/IL-2+) (FIG. 1B). The production of $Th_1$ CD4+ T-cells at this timepoint was correlated with an increase in IgG2c antibodies in the serum 21 days post-immunization (FIG. 2C). In contrast, total IgG and IgG1 titers in serum at day 21 were similar among all adjuvanted groups (FIGS. 2A and 2B). Examination of the neutralizing potential of the induced antibodies showed a correlation between the presence of IgG2c antibodies in the serum and increased neutralization potential; animals immunized with SLA-SE had the highest IgG2c titers and showed higher PRNT titers compared to those immunized with Alum or SE. Furthermore, high PRNT titers were induced even at greatly reduced WN-80E doses; the PRNT titers observed following immunization with 0.1 µg WN-80E+ SLA-SE were significantly greater (P<0.05) than those observed following immunization with 10 µg of protein in combination with Alum. Taken together, these results suggest that SLA-SE can increase the neutralizing antibody titer generated after a single injection with WN-80E, and that inclusion of the SLA agonist may allow up to 100 fold dose sparing of the antigen.

SLA Can Enhance the Protective Efficacy of WN-80E In Multiple Formulations.

Figures 3A, 3B, 3C, 3D:
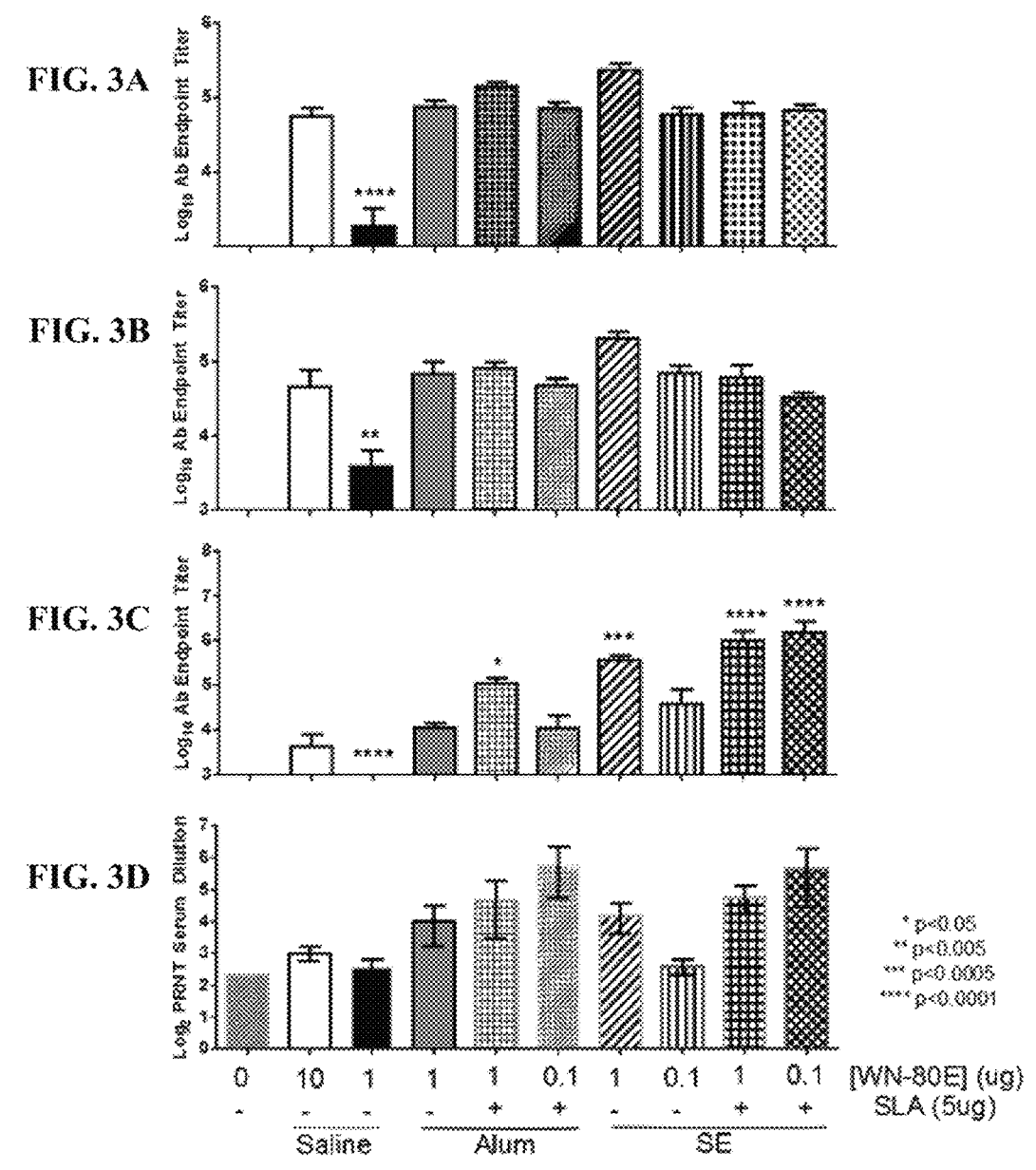

Given the increase in neutralizing antibodies induced by the combination of SLA and SE, we investigated whether or not addition of SLA could increase protective capacity when combined with the licensed adjuvant Alum. Mice were immunized with reduced amounts (either 1 µg or 0.1 µg) of antigen in combination with stable emulsion or Alum containing adjuvants via the intramuscular route. Two groups of mice were immunized. One group was euthanized 21 days following immunization to examine serum antibody responses to WN-80E, the second was challenged via the intra-peritoneal route with 100 $LD_{50}$ WNV (NY99 strain). Three days following challenge, serum was collected from all mice, and virus titers were determined by plaque assay. When compared with WN-80E alone, all adjuvanted groups induced similar levels of total serum IgG and IgG1 against WN-80E (FIG. 3A, 3B). As in the previous experiments, the inclusion of the SLA agonist adjuvant induced a significantly increased level of IgG2c when combined with both Alum and SE, as well as in a aqueous formulation (FIG. 3C). Those groups showing a significant increase in IgG2c titers also showed elevated PRNT titers at this timepoint (FIG. 3D). These results are consistent with previous findings, that SLA containing adjuvants show increased neutralizing potential, and that this is correlated with the induction of a Th1 antibody response characterized by increased levels of IgG2c. Furthermore, these studies demonstrate the formulation flexibility of SLA, demonstrating an increase in WNV neutralizing titers alone or when combined with Alum or SE formulations.

In a parallel study, the inventors investigated the ability of SLA containing adjuvants to protect animals from lethal WNV challenge following a single immunization in combination with WN-80E. Mice were immunized once with WN-80E combined with antigen, and challenged 21 days post-immunization. Following challenge, ail control mice succumbed to infection by day 10. Consistent with previous data utilizing WN-80E, mice immunized with antigen alone showed a 70% survival rate, while 80% of animals immunized with WN-80E combined with either SE emulsion alone or an aqueous formulation of SLA (SLA-AF) survived. All animals immunized with Alum, SLA-Alum or SLA-SE adjuvants survived challenge (FIG. 4A, 4B, Table 1). In addition to survival, examined the viral titers were examined 3 days following challenge. The adjuvants were clearly effective in reducing viral load (FIG. 4C). Animals immunized with 0.1 µg WN-80E and Alum or SE alone showed detectable titers in 70% and 30% of animals. Addition of SLA to SE reduced the number of animals with detectable titer to 10%, while addition of SLA to Alum resulted in no detectable virus titer in any animal at this time point. Collectively, these results demonstrate that addition of the TLR agonist SLA in formulations can enhance the protection of WN-80E antigen in mice by reducing virus titers to minimal or undetectable levels at a low antigen dose (0.1 µg) after only a single immunization.

SLA Induces an Increase in Germinal Center B-Cells and Pre Plasmablasts Following Immunization.

Figure 5A:
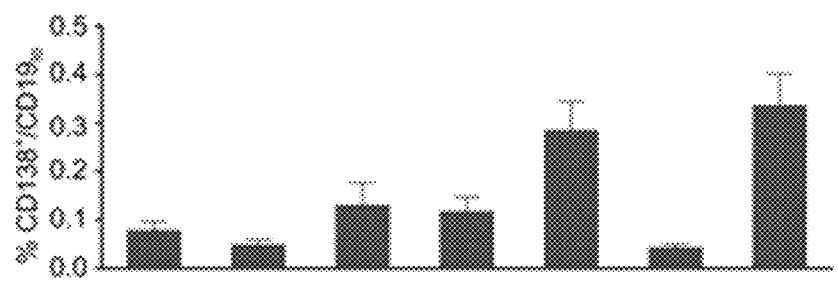
FIGS. 5A-5B are a series of graphical representations depicting various data relating to immunized animals in embodiments of the invention.
Figure 5B:
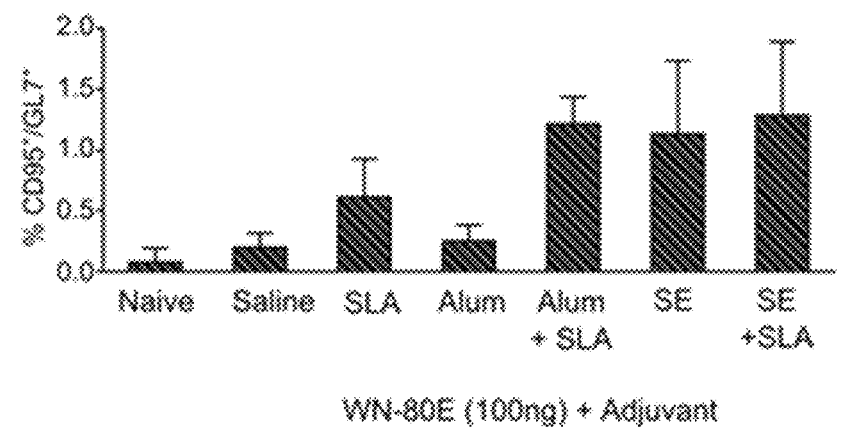

The previous experiments demonstrate the utility of the TLR-4 agonist SLA as an adjuvant for a single-shot WNV vaccine in multiple formulations, and suggest that the SLA- Alum and SLA-SE formulations may provide sterilizing immunity insofar as no virus could be detected in the majority of challenged animals. In an independent study, the inventors have further investigated the cellular correlates for reduction of d3 virus titers observed in a prior study. The ability of adjuvants to stimulate antibody producing cells following immunization was examined. Following a single immunization, an elevated number of CD138+B22010 pre-plasmablast cells in animals immunized with SLA containing adjuvants was observed (FIG. 5A). High levels of these cells are maintained following a boost injection in SLA-Alum and SLA-SE adjuvants (FIG. 5B). Animals immunized with SLA-SE or SLA-Alum also showed a strong induction of Th1 CD4+ T-cells following a prime immunization (FIG. 6). In addition, SLA-Alum, SE, and SLA-immunized mice showed increased CD95+/GL7+ germinal center (GC) cells in draining inguinal lymph nodes following two injections, suggesting that this subtype may correlate with reduction in virus titer (FIG. 5B).

Discussion

There are a number of WNV vaccines in pre-clinical or clinical stages of development, yet to date, none are available for human use. Live attenuated WNV vaccines based on the 17D strain of Yellow Fever virus have advanced the furthest in clinical trials; the vaccine has shown positive safety and immunogenicity profiles in Phase I and Phase II trials. However, as with all live attenuated vaccines, the ability of the vaccine vector to replicate in immunized subjects and potentially to cause disease during the viremic period remains a documented concern. Furthermore, live attenuated vaccines such as Yellow Fever pose a more significant risk to elderly and immunocompromised individuals, who are at greater risk for severe complications from WNV infection. In order to circumvent some of these safety concerns, a number of subunit vaccines based on the E protein have been developed. Of these, the WN-80E protein is the most clinically advanced, in a Phase I study, WN-80E was shown to be safe and immunogenic after 3 doses of 5 µg, 15 µg or 50 µg of protein adjuvanted with Alhydrogel® (Clinical Trial #: NCT00707642). While these results are promising, the overall level of virus neutralizing antibody induced by this vaccine was low relative to live attenuated vaccines. Furthermore, an ideal vaccine would provide sufficient protection after a single vaccine dose and would require less antigen, ultimately lowering the cost/dose. The primary goal of this study was to identify an adjuvant which may provide both dose and dosage sparing functions, ultimately enabling durable protection following a single dose of WN-80E antigen.

In pre-clinical development studies with WN-80E, 1 µg of protein was shown to be immunogenic in mice following two injections with the saponin based ISCOMATRIX® adjuvant. In this study, it is demonstrated that induction of PRNT titers in mice following a single injection of 0.1 µg of WN-80E in combination with SLA-SE. The level of neutralizing antibody following immunization, which serves as a correlate of protection for several other *Flavivirus* vaccines, was dependent on the presence of SLA, and was correlated with an increase in serum IgG2c titers. The induction of IgG2c antibodies is in turn dependent on induction of a Th1 CD4+ T-cell response by SLA, providing a mechanism for SLA mediated enhancement of protection that is consistent with studies investigating other vaccines. In an additional arm of this study, the response in all groups is boosted with an additional injection, and find that PRNT titers as well as IgG2c levels are increased in all adjuvanted groups (FIG. 7). This finding would suggest that one of the key functions of SLA is to accelerate the induction of neutralizing responses.

The enhancement of neutralizing antibody responses by SLA-SE prompted the inventors to examine the ability of SLA to enhance antigen specific responses in additional formulations. While emulsion based adjuvants (e.g., MF95, Novartis) are in use clinically in Europe, approval in the U.S. and other countries has been problematic to date. In order to initiate development of a vaccine formulation that may be advanced into clinical trials, SLA-Alum was focused on for two reasons. First, WN-80E has already shown promise in clinical trials in combination with Alum. Second, the SLA-Alum formulation utilized in this study is similar to AS04 (GlaxoSmithKline), which combines the TLR-4 agonist monophosphoryl Lipid-A (MPL), and which is licensed for use as a component of the HPV vaccine Cervarix®. The primary difference between SLA-Alum and AS04 is the use of a fully synthetic, rationally designed TLR-4 agonist (SLA) which has improved potency compared to a purified biological product (MPL) which is a mixture of compounds, only some of which are known to show TLR-4 agonism in humans. As with SLA-SE, SLA-Alum is capable of increasing the neutralizing antibody response following a single immunization with WN-80E, with the magnitude of the neutralizing response similar between SLA-SE and SLA-Alum at a low antigen dose.

As expected from previous studies, immunization with WN-80E increased survival of animals following challenge, a finding consistent with the relatively low lethality of WNV in murine models. However, adjuvants could be stratified based on their ability to reduce serum viral titer at early times post challenge. This ability is critically important, as early replication of WNV is correlated with increased neuroinvasion at later timepoints and serious disease. At lower antigen doses, immunization with Alum resulted in an average titer decrease of less than 10-fold relative to naive controls, with 70% of animals showing measurable virus titers. Addition of SLA to Alum resulted in undetectable virus in 100% of animals, which represents a decrease in titer of approximately 1000-fold relative to uninfected controls.

Collectively, our findings demonstrate the utility and formulation flexibility of SLA as an effective adjuvant for recombinant WNV vaccines, and that SLA induces a more potent and effective antibody response. In previous studies, the inclusion of a TLR-4 agonist was shown to increase the diversity of antibody variable regions following immunization with a malaria antigen suggesting a more rapid maturation of the antibody response which correlates with increased neutralization potential. Consistent with this mechanism, the inventors find an increased number of germinal center B-cells present in animals immunized with SLA containing adjuvants, suggesting that a more mature antibody response has developed following immunization with SLA-Alum or SLA-SE. In addition SLA-Alum and SLA-SE induce an increased number of CD138+CD19lo preplasmablast cells, which may contribute to the neutralizing antibodies observed after a single injection. Future studies which directly address the antibody diversity induced by these adjuvants will confirm this mechanism. In addition, characterization of novel antibodies may allow estimation of the percentage of antibodies produced which have neutralizing potential. Previous studies have mapped neutralizing antibodies to epitopes in DII and DIII in both WNV as well as other flaviviral E proteins in mice. However, more recent studies suggest that DIM antibodies may not play a critical role in neutralization in humans infected with other flaviviruses.

Another promising aspect of these results is the possibility of broadened protection against diverse flaviviruses induced by SLA-Alum or SLA-SE. Many studies have previously investigated cross-protection capability between flavivirus E-proteins, and have found that E-proteins from one virus can protect against other viruses in the genus. This cross protection is attributed to structural similarities between the E-proteins of members of a flavivirus serogroup. In previous studies with other viruses such as highly pathogenic avian influenza (HPAI), TLR-4 agonist adjuvants have been shown to increase protection not only to homologous virus, but also to antigenically distinct heterologous viruses. These findings, in combination with those presented here suggest the possibility that SLA containing adjuvants represent a tool to enhance protection against drifted flaviviral strains, such as the lineage 2 WNV viruses which are currently emerging in Europe. SLA based formulations may also be useful to enhance the protection across the four dengue virus (DENV) serotypes, where protection against the multiple serotypes is critical for an effective vaccine.

In summary, a clinical stage recombinant WNV antigen, WN-80E, was utilized to identify SLA adjuvant formulations capable of generating robust immune responses. The results demonstrate that robust responses can be generated after a single dose and these responses provide protection against virus challenge in the mouse model of West Nile Virus disease. Furthermore, it is demonstrated herein that SLA-Alum induces enhanced protection in mice when compared to Alum alone, as no virus was detected by the plaque method in any of the mice in the SLA-Alum group. Future work to optimize this formulation by investigating additional doses of SLA and routes of immunization will provide a foundation for advancement of this vaccine into additional models and future clinical studies. Ultimately, the use of SLA as an adjuvant may provide a more effective vaccine for this emerging public health threat and help to reduce the severity and size of future WNV outbreaks.

protein, which encodes receptor binding and fusion functions. Despite many promising E-protein vaccine candidates, there are currently none licensed for use in humans. This study reports the optimization of a WNV vaccine candidate containing a clinical-stage WNV recombinant E-protein antigen (WN-80E) and a TLR-4 agonist adjuvant containing a synthetic Lipid A TLR-4 agonist (SLA) and the saponin QS21. We have optimized a liposome formulation with these adjuvant components (LSQ) for rapid induction of potent antiviral immunity in murine models, and find that both SLA and QS21 individually stimulate the production of multi-functional $T_h1$ $CD4^+$ T-cells ($IFN\square^+/TNF\square^+/IL-2^+$), as well as an increase in the number of germinal center B-Cells ($CD95^+/GL7^+$) in a dose dependent manner. Consistent with induction of $T_h1$ biased cellular immunity, the humoral response following adjuvanted immunization in mice is focused toward production of class-switched IgG2c antibodies, resulting in high levels of virus neutralization activity. Importantly, we observe significantly increased neutralizing titers in mice given formulations which contain both SLA and QS21, compared to either component alone. Using an optimized vaccine formulation, we demonstrate induction of durable immunity (300 days) following a single immunization in mice, and stimulation of functional protective immunity in a Syrian hamster challenge model of WNV disease. Taken together, these studies demonstrate the utility of LSQ adjuvant formulations for induction of functional and durable immunity for recombinant subunit protein vaccines for flaviviruses.

Data pertaining to in-vivo efficacy of the LSQ vaccine as well as vaccine development is set forth in the Figures which are attached herein.

Example 3

Clinical Testing of West Nile LSQ Vaccine

The vaccine described herein will be tested in a clinical trial. The Phase 1, open-label, clinical study of WN-80E formulated with liposomes+SLA and WN-80E formulated

TABLE 1

Survival and Viral Titers Following WNV Challenge

| Antigen | Dose (Hg) | Adjuvant | Survival | Animals With Detectable Virus Titer (%) | Day 3 Virus Titer Average | (Range) |
|---|---|---|---|---|---|---|
| None | 0 | None | 0/10 | 100 | $3.2 \times 10^4$ | ($3 \times 10^3$-$5 \times 10^4$) |
| WN-80E | 1 | None | 7/10 | 100 | $7.1 \times 10^3$ | ($2 \times 10^2$-$5 \times 10^4$) |
| WN-80E | 0.1 | Alum | 10/10 | 70 | $5.1 \times 10^3$ | (<100-$2.9 \times 10^4$) |
| WN-80E | 0.1 | SLA | 8/10 | 40 | $3.7 \times 10^2$ | (<100-$2.9 \times 10^4$) |
| WN-80E | 0.1 | Alum + SLA | 10/10 | 0 | $5.0 \times 10^1$ | (<100) |
| WN-80E | 0.1 | SE | 8/10 | 30 | $5.7 \times 10^2$ | (<100-$4.9 \times 10^4$) |
| WN-80E | 0.1 | SE + SLA | 10/10 | 10 | $9.5 \times 10^1$ | (<100-$5 \times 10^2$) |

Example 2

A Recombinant West Nile Virus Vaccine Antigen Formulated with a Combination of a Synthetic TLR-4 Agonist and a Saponin Adjuvants Induces a Robust and Durable Immunity West Nile virus (WNV) is a mosquito-transmitted member of the Flaviviridae family that has emerged in the $21^{st}$ century to become a public health threat. Given the sporadic nature of WNV epidemics both temporally and geographically, there is an urgent need for a vaccine that can rapidly provide effective immunity. Protection from WNV infection is correlated with antibodies to the viral envelope (E)

with liposomes+SLA+QS21 (LSQ) in healthy adult volunteers will be evaluated at different dose levels of each of the vaccine's WN-80E component with the same amount of SLA and additional adjuvant or the highest dose level of WN-80E without SLA and adjuvant. Subjects will receive a single IM injection of study vaccine at weeks 0 and 4.

Safety and tolerability will be assessed throughout the study by targeted physical examination, routine laboratory testing (hematology, clinical chemistry and urinalysis) and the recording of vital signs and adverse events in study volunteers. In addition, subjects will use diary cards for 14+/−2 days after each vaccination to record reactogenicity and tolerance data as well as specific adverse events. Efficacy assessments in this study will include the determination of the rate and extent of virus neutralizing antibody titers (i.e., functional immunogenicity), as determined by PRNT$_{50}$ (plaque reduction neutralization test) assay of >1:10.

The inventors expect the vaccine to be well tolerated with no severe adverse events throughout the dosing period. Additionally, the vaccine is expected to be effective and confer a sufficient protective immune response to WNV mediated disease.

CONCLUSIONS

We have defined an adjuvant formulation (SLA-LSQ) by systematic investigation/optimization of all bioactive components in murine models. WN-80E+SLA-LSQ has been shown to be effective following delivery by a number of immunization routes (i.m., s.c., i.n.). WN-80E+SLA-LSQ provides durable immunity, with protective antibody titers observed in murine models up to 300 days following a single immunization. We have established protective and non-protective doses of WN-80E in murine and hamster models in order to quantify adjuvant induced dose sparing. We have established the contribution of all adjuvant components to survival in a murine model following prime-boost immunization with low levels (10ng) of WN-80E.

Although the invention has been described with reference to the above examples, it will be understood that modifications and variations are encompassed within the spirit and scope of the invention. Accordingly, the invention is limited only by the following claims.

What is claimed is:

1. A vaccine comprising:
   a) an effective amount of purified West Nile virus envelope ("E") polypeptide, wherein the E polypeptide constitutes approximately 80% of the length of wild type E starting from amino acid residue 1 at its N-terminus; and
   b) an effective amount of a Toll-like receptor 4 (TLR-4) agonist; and
   c) an effective amount of a purified saponin adjuvant,
   wherein the TLR-4 agonist and the saponin are combined to form a liposome formulation, and
   wherein the vaccine induces the production of neutralizing antibodies in human subjects.

2. The vaccine of claim 1 wherein the E polypeptide is recombinantly produced and expressed in insect host cells.

3. The vaccine of claim 1 wherein the E polypeptide is recombinantly produced and expressed in *Drosophila melanogaster* Schneider 2 (S2) host cells.

4. The vaccine of claim 1, wherein the E polypeptide is secretable into growth medium when expressed recombinantly in a host cell.

5. The vaccine of claim 1, wherein the TLR-4 agonist is a synthetic MPL and the saponin adjuvant is purified from the extract of Soap Bark tree *Quillaja saponaria*.

6. The vaccine of claim 5, wherein the TLR-4 agonist is a synthetic lipid A (SLA).

7. The vaccine of claim 5, wherein the saponin adjuvant is QS-21.

8. The vaccine of claim 1, further comprising a pharmaceutically acceptable excipient.

9. The vaccine of claim 1, for use in an immunodeficient subject.

10. The vaccine of claim 9, wherein the vaccine contains an effective amount of purified E protein as set forth in SEQ ID NO:2.

11. The vaccine of claim 1, formulated in dosage form of about 0.5-20 ug per dose.

12. A method for raising a protective immune response in a subject, comprising administering to the subject a therapeutically effective amount of the vaccine of claim 1 to the subject, thereby raising a protective immune response in the subject.

13. A method of providing immune protection in a subject against West Nile virus induced disease comprising administering an effective amount of the vaccine of claim 1 to the subject, thereby providing protection from West Nile disease.

14. A method for raising a protective immune response in a subject, comprising administering to the subject a therapeutically effective amount of the vaccine of claim 10 to the subject, thereby raising a protective immune response in the subject.

15. A method of providing immune protection in a subject against West Nile virus induced disease comprising administering an effective amount of the vaccine of claim 10 to the subject, thereby providing protection from West Nile disease.

16. A vaccine comprising:
   an effective amount of purified protein of SEQ ID NO: 2;
   an effective amount of a synthetic lipid A (SLA) adjuvant; and
   an effective amount of the purified saponin QS21 adjuvant,
   wherein the SLA and QS21 adjuvant are combined to form a liposome formulation (LSQ), and
   wherein the vaccine induces the production of neutralizing antibodies in human subjects.

* * * * *